United States Patent [19]

Underiner et al.

[11] Patent Number: 5,521,315
[45] Date of Patent: May 28, 1996

[54] OLEFIN SUBSTITUTED LONG CHAIN COMPOUNDS

[75] Inventors: Gail Underiner, Brier; David Porubek, Seattle; J. Peter Klein, Vashon; Elisa Eiseman, Seattle; Alistair Leigh, Brier; Anil Kumar; John Michnick, both of Seattle, all of Wash.

[73] Assignee: Cell Therapeutics, Inc., Seattle, Wash.

[21] Appl. No.: 59,697

[22] Filed: May 10, 1993

Related U.S. Application Data

[63] Continuation-in-part of Ser. No. 3,372, Jan. 12, 1993, Pat. No. 5,354,756.

[51] Int. Cl.$^6$ .................. C07D 211/88; C07D 239/80
[52] U.S. Cl. .................. 546/243; 546/242; 544/285
[58] Field of Search .................. 548/545, 546, 548/547; 546/243; 544/285

[56] References Cited

U.S. PATENT DOCUMENTS

| | | | |
|---|---|---|---|
| 3,278,526 | 10/1966 | Louthan et al. | 548/545 |
| 3,883,342 | 5/1975 | Abramitis et al. | 548/545 |
| 4,171,302 | 10/1979 | Abblard et al. | 548/545 |
| 4,396,516 | 9/1983 | Kinoshita et al. | 252/51.5 |
| 4,612,132 | 9/1986 | Wollenberg et al. | 548/545 |
| 4,824,851 | 4/1989 | Takaya et al. | 514/274 |
| 4,879,296 | 11/1989 | Daluge et al | 514/263 |
| 4,997,594 | 3/1991 | Walsh | 548/545 |
| 5,208,240 | 5/1993 | Peet et al. | 514/263 |
| 5,223,504 | 6/1993 | Noverola et al. | 514/263 |
| 5,272,153 | 12/1993 | Mandell et al. | 514/263 |
| 5,281,605 | 1/1994 | Kis et al. | 514/263 |

FOREIGN PATENT DOCUMENTS

| | | |
|---|---|---|
| 820325 | 8/1969 | Canada . |
| 89/1093571 | 5/1987 | Japan . |

OTHER PUBLICATIONS

Rama Rao et. al. Tetrahedron Letters vol. 32, No. 34 p. 4395, 1991.

*Primary Examiner*—Mukund J. Shah
*Assistant Examiner*—Pavanaram K. Sripada
*Attorney, Agent, or Firm*—Stephen Faciszewski; Jeffrey B. Oster

[57] ABSTRACT

There is disclosed an olefin-substituted compound having the formula:

R—(core moiety), wherein R is a straignt chain hydrocarbon having at least one double bond and a carbon chain length of from about 6 to about 18 carbon atoms, wherein multiple double bonds are separated from each other by at least three carbon atoms, wherein the closest double bond to the core moiety is at least five carbon atoms from the core moiety, and wherein the hydrocarbon chain may be substituted by a hydroxyl, halo, keto or dimethylanimo group and/or interrupted by an oxygen atom and salts thereof and pharmaceutical compositions thereof.

7 Claims, 22 Drawing Sheets

5,521,315

OLEFIN SUBSTITUTED LONG CHAIN COMPOUNDS

CROSS REFERENCE TO RELATED PATENT APPLICATION

This application is a continuation-in-part application from U.S. patent application Ser. No. 08/003,372 filed Jan. 12, 1993 now U.S. Pat. No. 5,354,756.

TECHNICAL FIELD OF THE INVENTION

The invention relates to a class of olefin substituted long chain compounds that are effective agents to modulate cellular responses to noxious or inflammatory stimuli, or to directly be antimicrobial to yeast or fungal infections, or useful for the treatment and prevention of asthma. More specifically, the inventive compounds have at least one olefin group within a long chain hydrocarbon bonded to a ring nitrogen of a core moiety. The inventive compounds are useful antagonists to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,307 and 3,737,433. Metabolites of PTX were summarized in Davis et al., *Applied Environment Microbial.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947. In addition, U.S. Pat. Nos. 4,833,146 and 5,039,666 disclose use of tertiary alcohol analogs of xanthine for enhancing cerebral blood flow.

Furthermore, U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and that can maintain cellular homeostasis in the face of a variety of inflammatory stimuli. The present invention was made in a process of looking for such compounds.

SUMMARY OF THE INVENTION

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of a class of olefin long hydrocarbon chain substituted heterocyclic compounds. The inventive compounds are effective in modulating cellular response to external or in situ primary stimuli, as well as to specific modes of administration of such compounds in effective amounts.

The inventive compounds comprise compounds and pharmaceutical compositions having the formula:

R—(core moiety), wherein R is a straight chain hydrocarbon having at least one double bond and a carbon chain length of from about 6 to about 18 carbon atoms, wherein multiple double bonds are separated from each other by at least three carbon atoms, wherein the closest double bond to the core moiety is at least five carbon atoms from the core moiety, and wherein the hydrocarbon chain may be substituted by a hydroxyl, halo, keto or dimethylanimo group and/or interrupted by an oxygen atom. Preferably, each double bond (with the exception of a terminal olefin) is in a cis configuration.

Preferably, the core moiety has from one to three, five to six membered ring structures in a predominantly planar structure. There can be from one to about three R substituents on each core moiety. Preferably, the olefin substituent (R) is bonded to a ring nitrogen if one exists. For example, the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, 1-methyl-2,4(1H,3H)-quinazolinedione(1-methylbenzoyleneurea), 6-aminouracil, homophthalimide, succinimide, 1,3-cyclohexanedione, resorcinol, 1,3-dihydroxynaphthlene, 1,3-cyclopentanedione, 1,3-dimethyldihydroxypyrazolo[4,3-d]pyrimidine, 5-substituted uracils, 6-substituted uracils, 1-methylpyrrolo[2,3-d]pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4(3H)-one, most preferably, the heterocyclic core is a xanthine. The core moiety can also include a non-cyclic group. Examples of non-cyclic core groups include open chain analogs of glutarimide, carboxilic acid, a hydroxyl group, sulfone, sulfonate, and the like.

The present invention further provides a pharmaceutical composition comprising an inventive compound and a pharmaceutically acceptable excipient, wherein the pharmaceutical composition is formulated for oral, parenteral or topical administration to a patient.

The present invention further provides a method for treating an individual having a variety of diseases, wherein the disease is characterized by or can be treated by inhibiting an immune response or a cellular response to external or in situ primary stimuli, wherein the cellular response is mediated through a specific phospholipid-based second messenger acting adjacent to the inner leaflet of the cell membrane of a cell. The second messenger pathway is activated in response to various noxious or proliferative stimuli characteristic of a variety of disease states and the biochemistry of this second messenger pathway is described herein. More specifically, the invention is directed to methods in order to treat or prevent clinical symptoms of various disease states or reduce toxicity's of other treatments by inhibiting cellular signaling through the second messenger pathway described herein. The disease states or treatment-induced toxicity's are selected from the group consisting of proliferation of tumor cells in response to an activated oncogene; hematocytopenia caused by cytoreductive therapies; autoimmune diseases caused by a T cell response, monocyte response or a B cell response and antibody production; acute inflammatory disease such as septic shock or hemmoragic shock; resistance of mesenchymal cells to tumor necrosis factor (TNF); chronic inflammatory disease characterized by T cell, glial, astrocyte or monocyte adhesion, migration and/or release of inflammatory stimuli and metalloproteases, such as rheumatoid arthritis, osteoarthritis, multiple sclerosis or insulin dependent diabetes mellitus (IDDM); proliferation of smooth muscle cells endothelial cells, fibroblasts and other cell types in response to growth factors, such as PDGF-AA, BB, FGF, EGF, etc. (i.e., atherosclerosis, restenosis, stroke, and coronary artery disease); human immunodeficiency virus infection (AIDS and AIDS related complex); proliferation of kidney mesangial cells in response to IL-1 Mip-1α, PDGF or FGF; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drug or radiation); enhancing antitumor effects of nonalkylating antitumor agents; intimation in response to inflammatory stimuli (e.g., TNF, IL-1 and the like) characterized by production of metalloproteases or allergies due to degranulation of mast cells and basophils in response to IgE or RANTES; bone diseases caused by overproduction of osteoclast-activating factor (OAF) by osteoclasts; CNS diseases caused by reduced signal transduction of the neurotransmitters epinephrine and acetylcholine; and combinations thereof. The inventive compounds are also useful as antimicrobial agents to directly treat fungal or yeast infections and to indirectly treat bacterial or viral infections through an immune stimulation and pro-hematopoietic effect, both mediated by the second messenger pathway described herein.

BRIEF DESCRIPTION OF THE DRAWINGS

Figure 12:
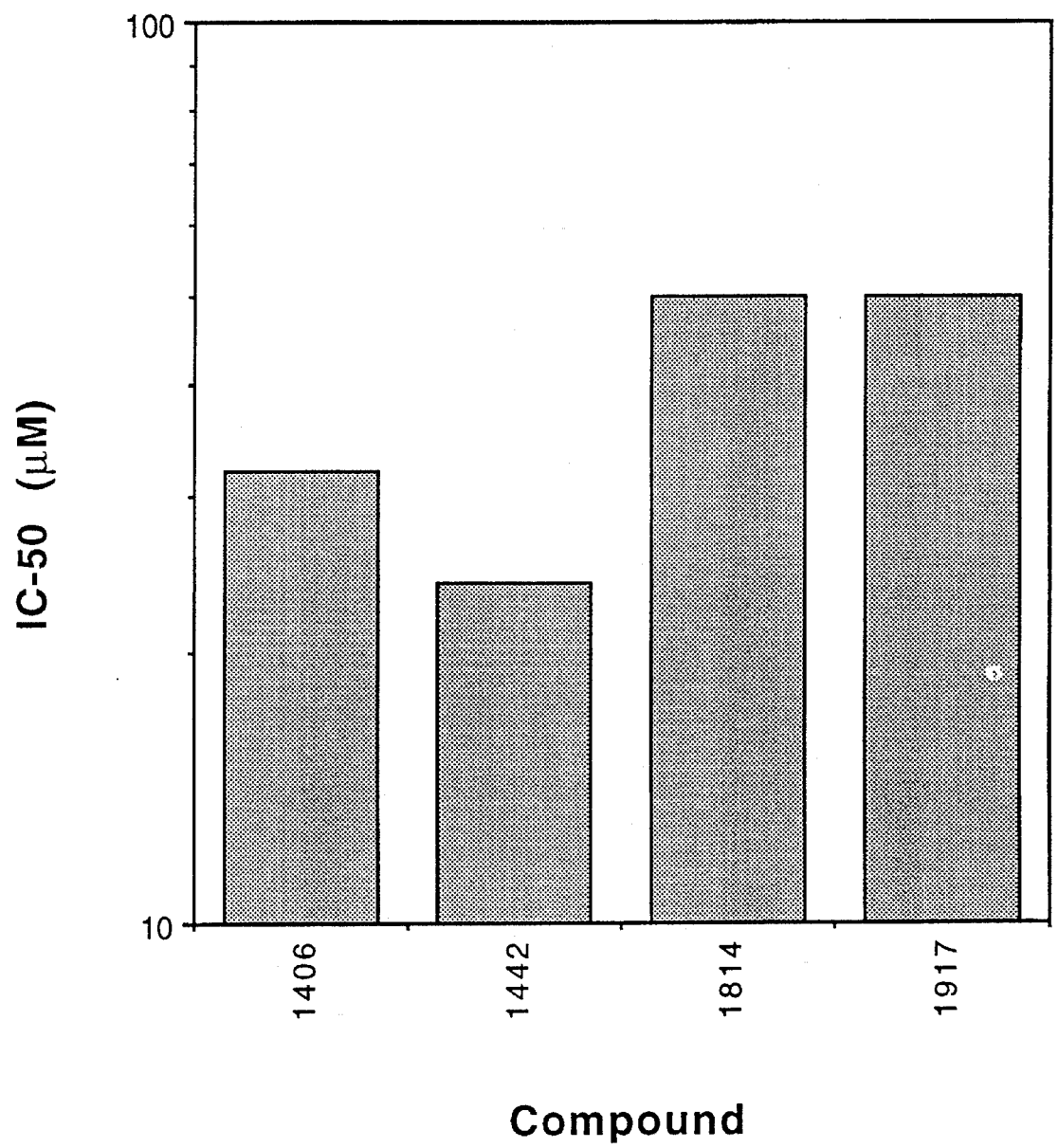

FIG. 12 shows the effects of four inventive compounds to inhibit proliferation of human lymphocytes in an IL-2 induced blastogenesis in vitro assay. This human in vitro assay is a human model for immune suppression activity to screen for drugs that would be beneficial in preventing organ rejection in organ transplantation. Briefly, human lymphocytes are obtained from blood from normal volunteers and plated into wells at $2 \times 10^5$ cells/well. Human IL-2 (40 U/well or 5 μl of a 100 U/ml solution) and drug at various concentrations are added to each well. The cells are incubated for six days and then proliferation is determined by a standard tritiated thymidine incorporation procedure. Cyclosporin A does not show significant activity in this in vitro assay. However, both CT1406 and CT1442 were active, as is shown by IC50 values in FIG. 12.

Figure 13:
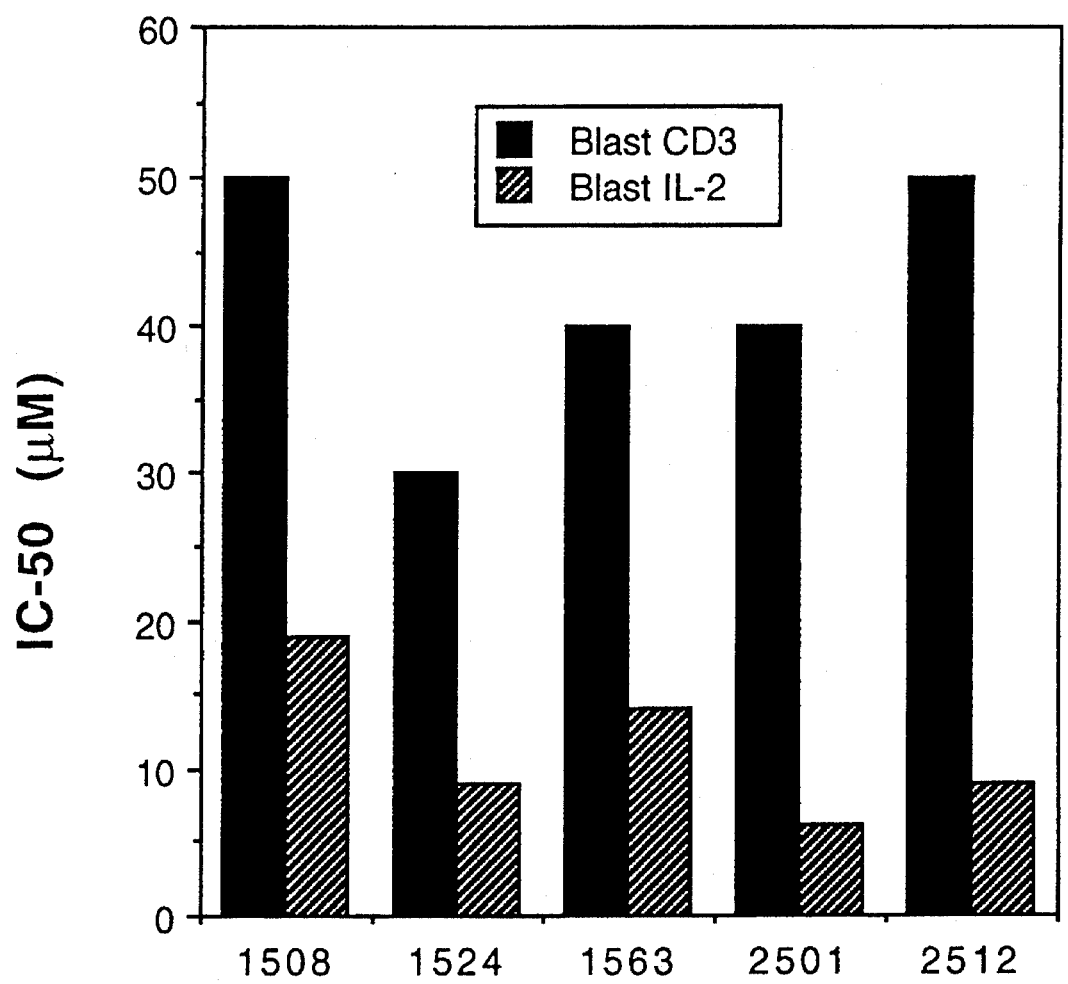

FIG. 13 shows various IC50 values of five inventive compounds as determined by an IL-2 blastogenesis assay described above or a CD3 blastogenesis assay. The CD3 blastogenesis assay is virtually identical to the IL-2 blastogenesis assay described herein, except a human anti-CD3 monoclonal antibody (4 μg/ml, Boehinger Manheimm) is used instead of human IL-2 and the cells are incubated for only three days. Again, Cyclosporin A is generally not very active in this in vitro assay. However, as shown in FIG. 13, several inventive compounds, including CT1524, CT2501 and CT2512, showed significant immune suppressing activity in these in vitro assays.

Figure 14:
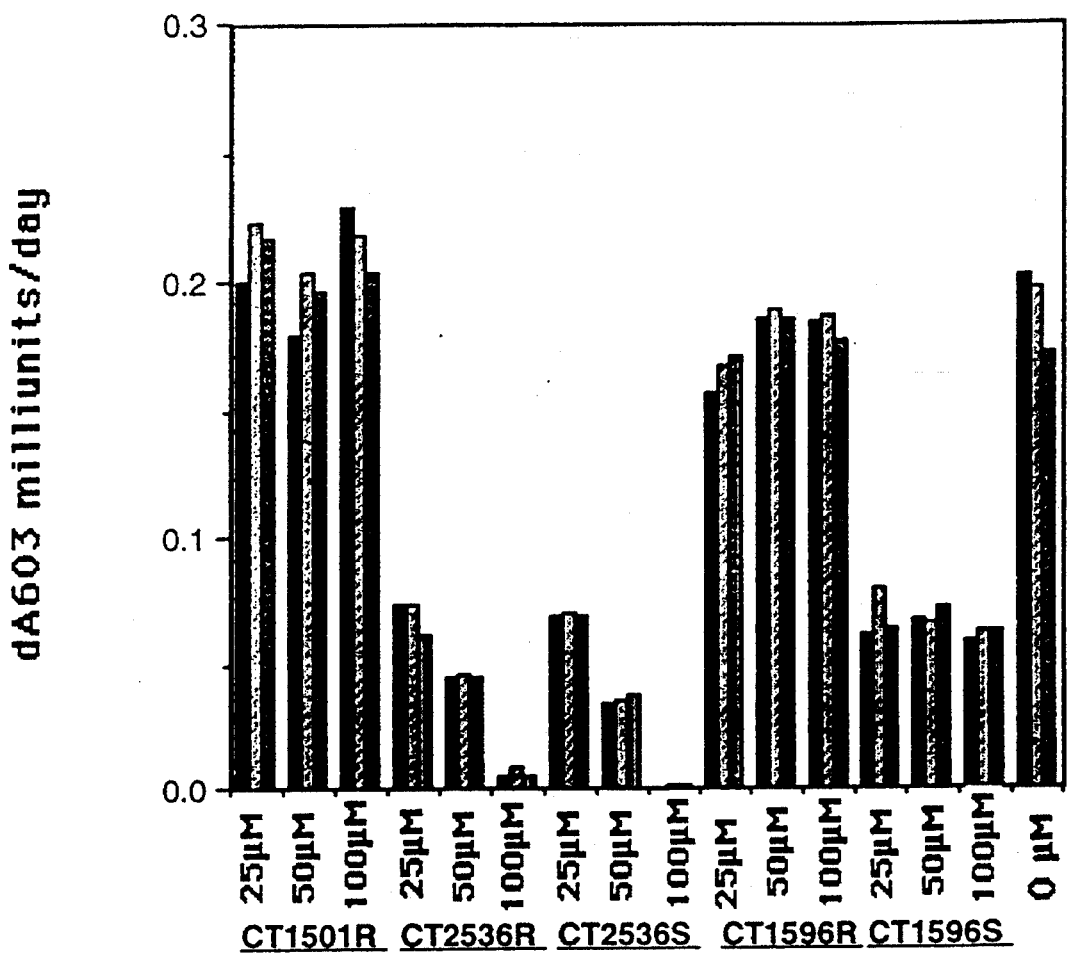

FIG. 14 shows the effects of CT2501R (a reference compound), CT2536R, CT2536S, CT1596R, and CT1596S of yeast growth (*Saccromyces cerevasie*) in the presence or absence of drug. These assays measure anti-yeast and anti-fungal activity of the drugs tested. As shown in FIG. 14, both the R and S enantiomers of CT2536 strongly inhibited yeast growth. Therefore either the R enantiomer, the S enantiomer or a racemic mixture of CT2536 are potential topical or systemic antimicrobial drugs. It should be noted that there was enantiomeric selectivity for CT1596.

Figure 15:
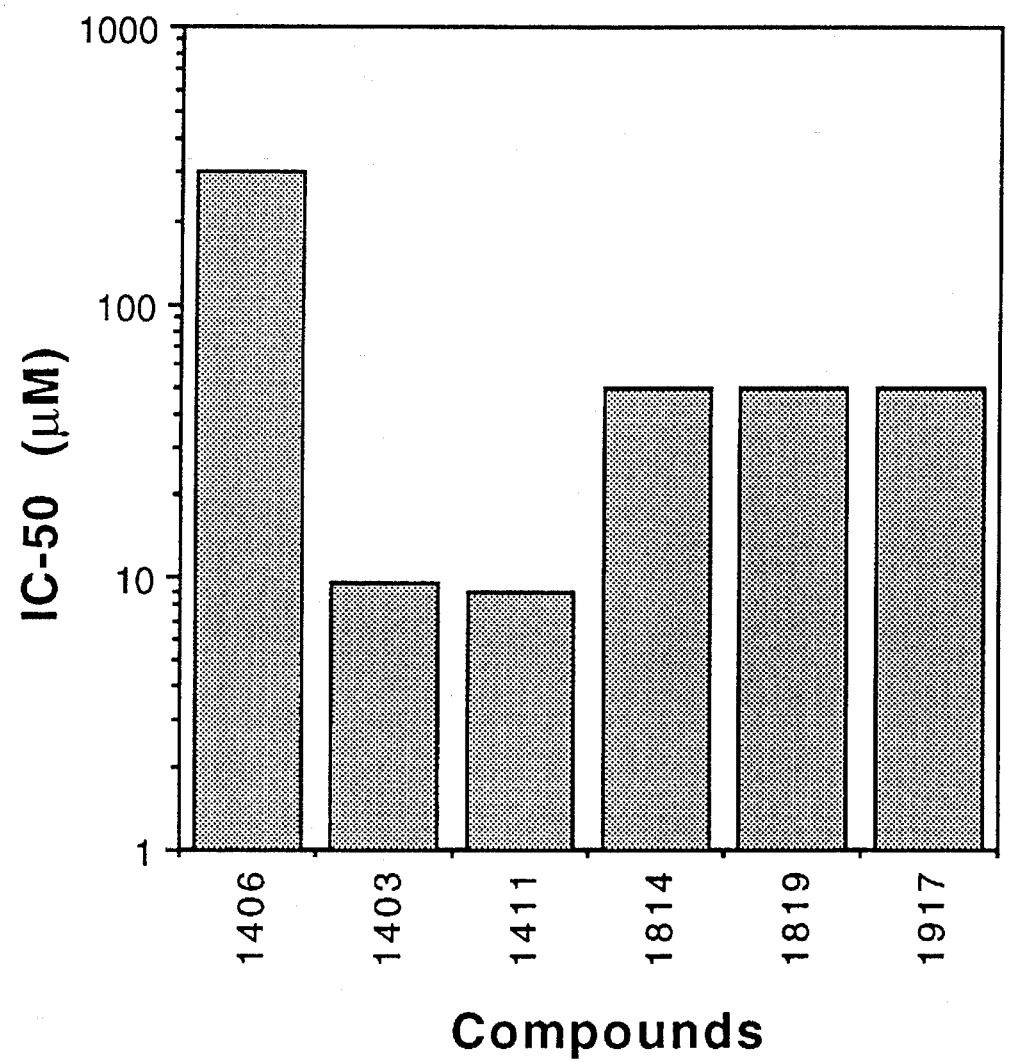

FIG. 15 illustrates the ability of six inventive compounds to inhibit proliferation of human stromal cells when stimulated with PDGF. This assay is an in vitro model for restenosis and treatment of atherosclerosis and coronary artery disease. Stromal cells were starved in serum-free media for one day and then stimulated with 50 ng/ml PDGF-BB. The drugs were added at the indicated concentrations one hour prior to PDGF stimulation. Tritiated thymidine was added for one day at the time of PDGF stimulation and the cells were harvested and counted by liquid scintillation counting 24 hrs later. Background counts (i.e., starved cells) were approximately 1% of control levels. FIG. 15 shows that all drugs were active in this predictive in vitro model, however CT1403 and CT1411 had IC50 values (μM) less than 10.

Figure 16:
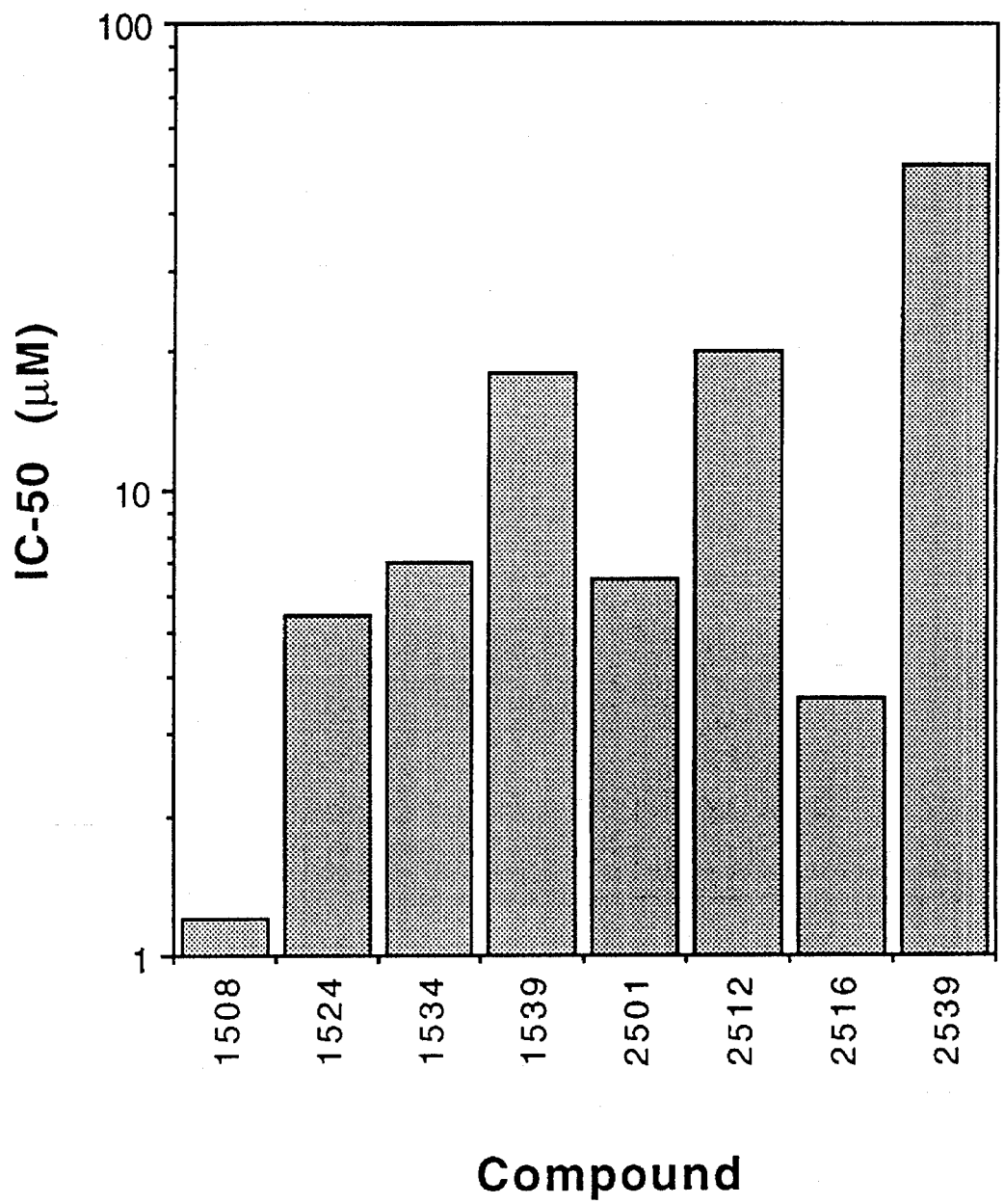

FIG. 16 illustrates the ability of eight inventive compounds to inhibit proliferation of human stromal cells when stimulated with PDGF. Background counts (i.e., starved cells) were approximately 1% of control levels. FIG. 16 shows that all drugs were active in this predictive in vitro model, however, CT1508 was most potent with an IC50 value less than 2 μM showing promise as a restenosis and reperfusion injury drug.

Figure 17:
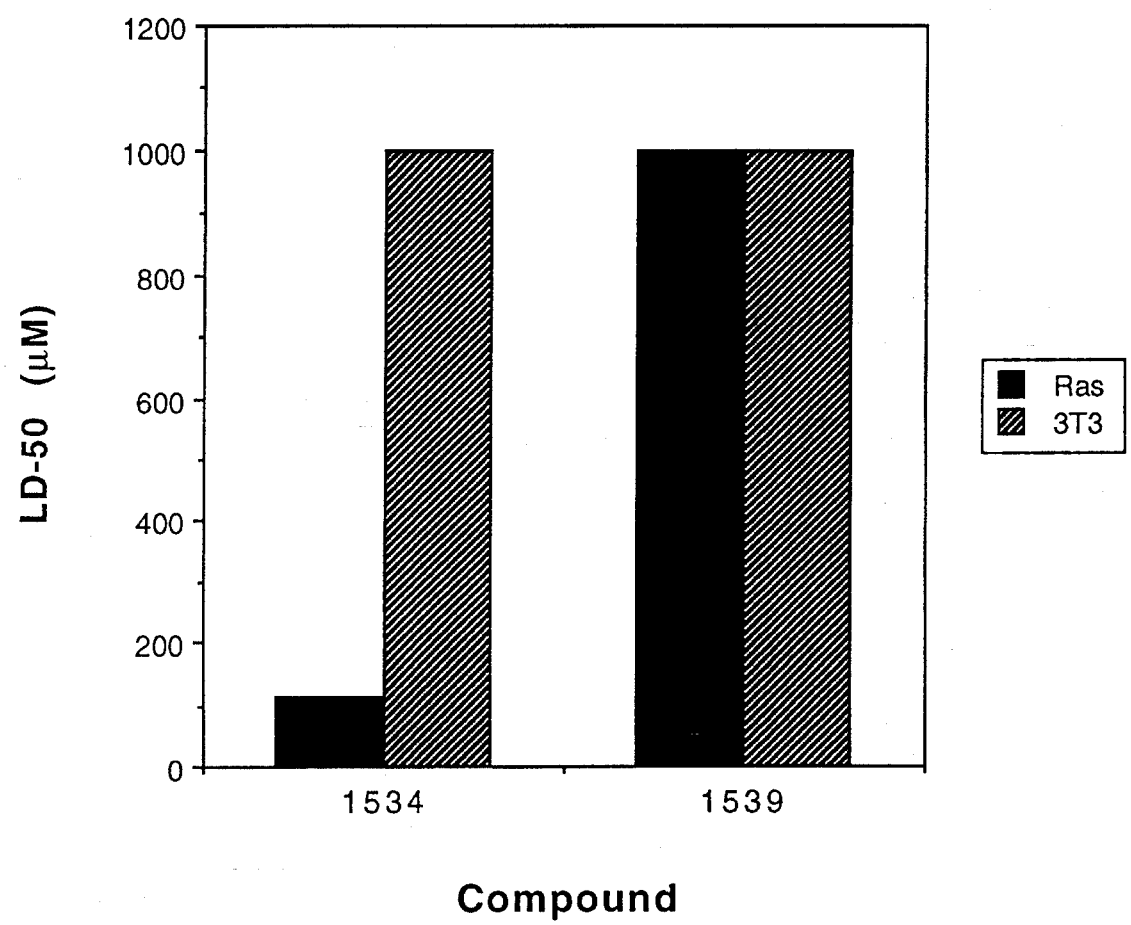

FIG. 17 shows a comparison of cytotoxicity determinations for CT1534 and CT1539 in transformed cells (Ras 3T3) and in normal 3T3 cells to determine the in vitro LD50 value in both cell types and to look for differential cytotoxicity effects between the cell types. CT1534 was much more cytotoxic for the transformed cell than the normal cell indicating differential toxicity for tumor cells and potential usefulness as a cancer chemotherapeutic agent. CT1539 appeared to be equally cytotoxic for both cell types.

Figure 18:
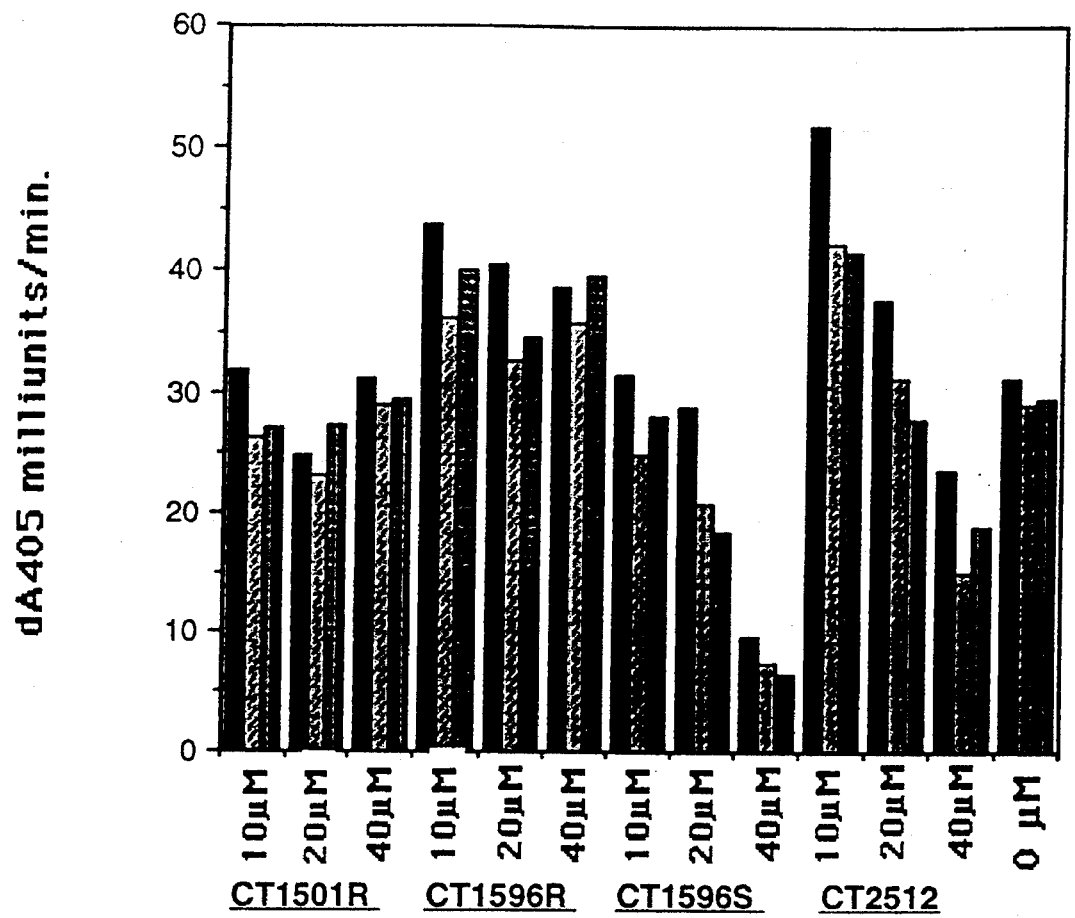

FIG. 18 illustrates data regarding proliferative activity of various inventive compounds for inducting CMV promoter activity. The CMV promoter assay measures gene transcription and translation activity wherein any active compounds will have cytotoxic activity to inhibit cellular protein synthesis machinery in transformed (adenovirus) cells. Each compound was tested and the data is listed in FIG. 18. CT1596S was the most cytotoxic compound tested.

Figure 19:
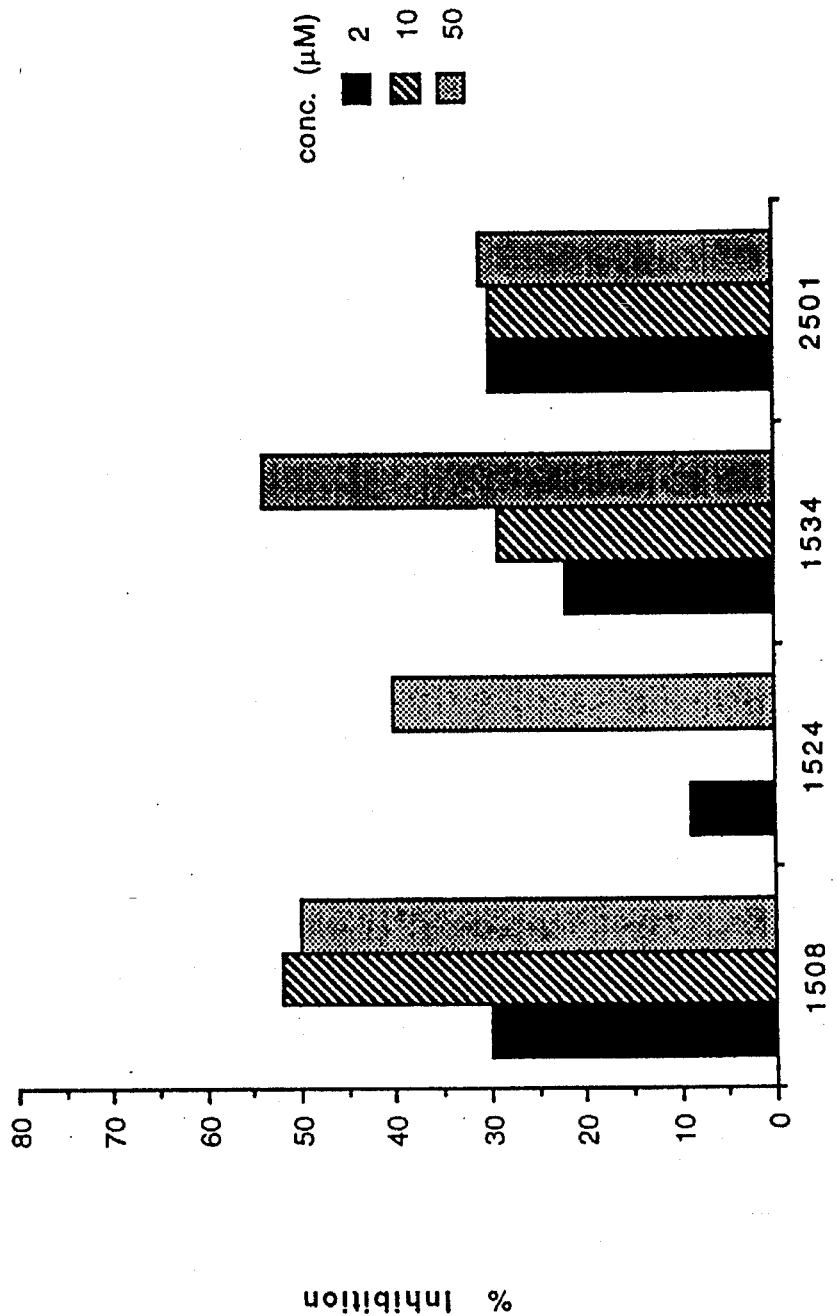

FIG. 19 illustrates a comparative experiment comparing CT1508, CT1524, CT1534 and CT2501 in an ex vivo human TNF model described herein. This assay is a predictive model for treatment and prevention of septic shock and sepsis syndrome. This model adds LPS to whole blood (normal human volunteers) to trigger a dose-dependent synthesis and extracellular release of TNF according to Desch et al. (*Lymphokine Res.* 8:141, 1989). The ex vivo model examines whether LPS-mediated release of TNF from monocytes in whole blood can be blocked by an inventive compound. CT1508 was the most effective agent in this ex vivo model for sepsis at lower doses that are likely achievable in vivo.

Figure 20:
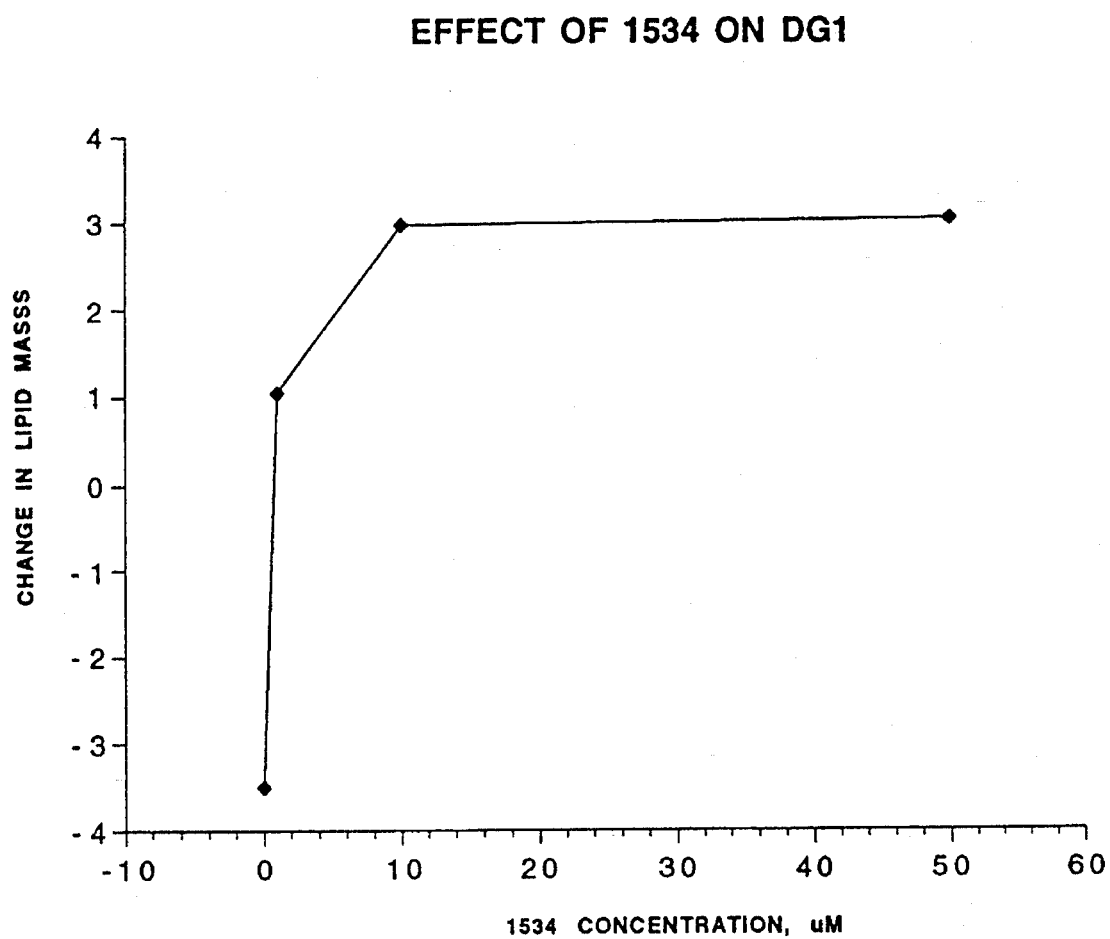
Figure 21:
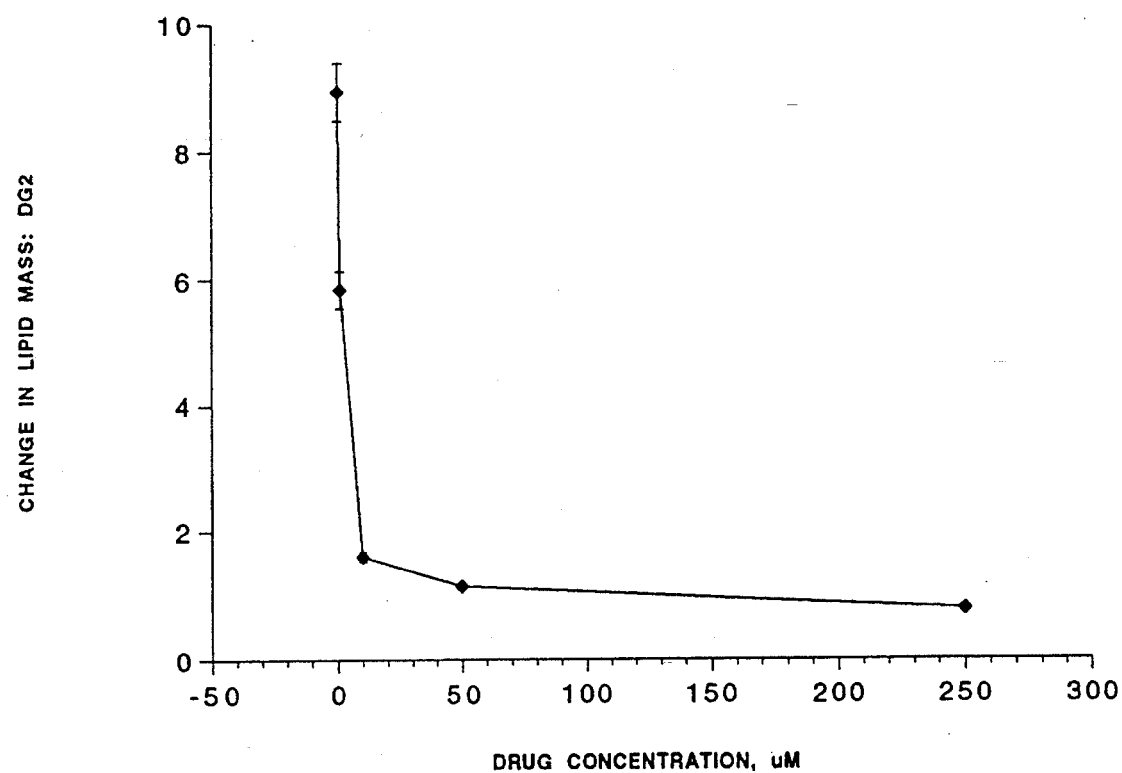
Figure 22:
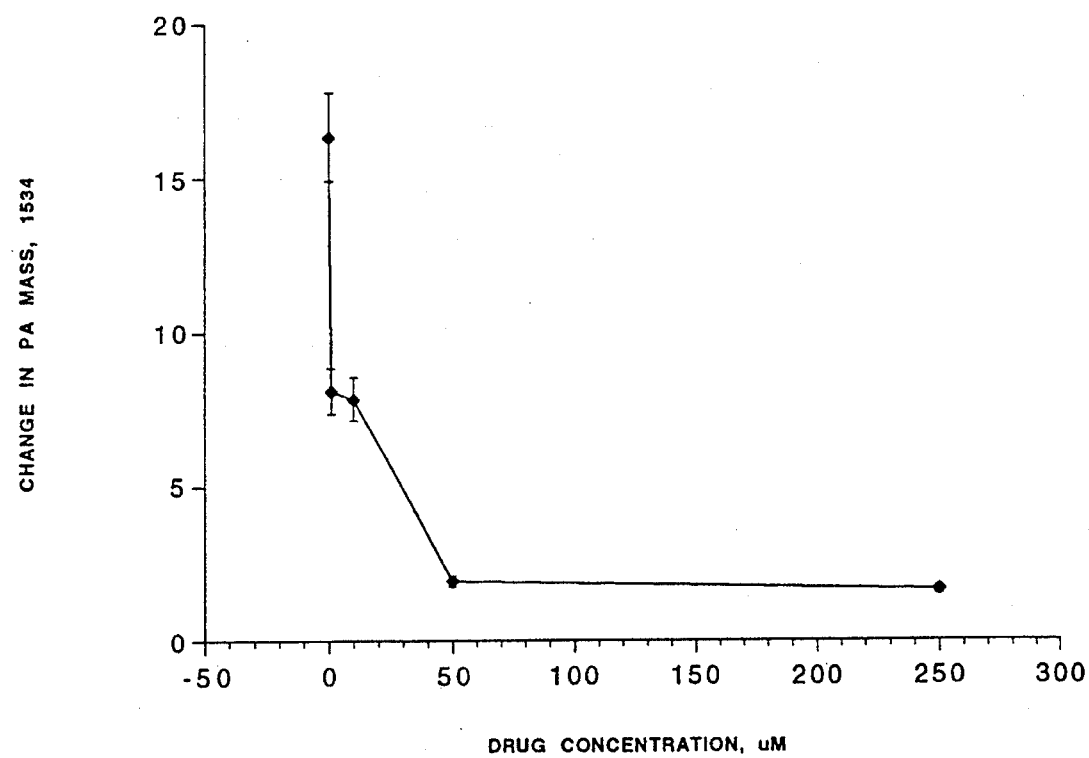

FIGS. 20–22 illustrate the effect of one inventive compound (CT1534) on the substates and products of the present second messenger pathway. Various concentrations of CT1534 were incubated with P388 cells (a murine monocyte/macrophage line) and changes in lipid mass determined at 0 time, 30 seconds and 60 seconds after signal stimulation. FIGS. 20–22 show the 30 second time point for two DAG peaks and a PA peak. This data shows that CT1534 inhibits the enzymes involved in second messenger signaling to an inflammatory stimulus in a dose-response fashion with a plateau of around 10 μM.

DETAILED DESCRIPTION OF THE INVENTION

The invention is directed to a defined genus of inventive compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with 1-saturated, 2-linoleoyl or 1,2-dioleoyl, dioleoy/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI, but rather derives from a PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography, gas-liquid chromatography or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA-2, followed by sn-2 transacylation by LPAAT, and a PLD-pathway from PA that is generated from either PE or PC or both substrates by PLD.

A method described here permits differentiation of the various subspecies of PA and DAG based upon acyl chain composition. This can differentiate those compounds that activate (and inhibit activation of) the present second messenger pathway from other pathways, such as the classical PI pathway. The present second messenger pathway involves substrates with unsaturated fatty acids in the sn-2 position other than arachidonate and those sub-species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates. Therefore, the inventive compounds are preferably, substantially enantiomerically pure, and preferably are the R enantiomer at the chiral carbon atom bonded to the hydroxyl group.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway is not inhibited by the inventive compounds or PTX. In PTX-treated cells, DAG derived from remodeled and PLA-generated PA is diminished (e.g., 1,2-sn-dioleoyl DAG, 1-alkyl,2-linoleoyl DAG and 1-alkyl,2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific inhibition of activation of the specific second messenger pathway that is activated primarily by various noxious stimuli, provides the inventive compounds with an ability to be used to treat a wide variety of clinical indications. Moreover, the in vitro and in vivo data presented herein provides predictive data of a wide variety of clinical indications that share a common thread of activation of the specific second messenger pathway, whose activation by noxious stimuli mediated through, for example, inflammatory cytokines, is specifically inhibited by the inventive compounds. In fact, it is this mechanism of action of the inventive compounds that explains why the inventive compounds can have a wide variety of different clinical indications. Activation of the present second messenger pathway is a major mediator of response to noxious stimuli and results in cellular signals that lead to, for example, inflammation, immune response, inhibition of blood cell regeneration and cancer cell growth. However, not all inhibitors inhibit all enzymes of this second messenger pathway. The inventive compounds are most effective mediators of inflammation and inhibition of blood cell regeneration. Signals mediated by the present second messenger pathway include, for example, those cellular responses of LPS directly, T cell activation by antigen, B cell activation by antigen, cellular responses to IL-1 mediated through the IL-1 Type 1 receptor (but not the IL-1 Type 2 receptor), the TNF Type 1 receptor, activated oncogenes (e.g., ras, abl, her2-neu and the like), low affinity GM-CSF (granulocyte macrophage colony stimulating factor) receptor, and smooth muscle cell proliferation stimulated by PDGF, b-FGF and IL-1. There are other signals that are not mediated through the present second messenger pathway, and these include proliferation of hematopoietic cells induced by G-CSF (granulocyte colony stimulating factor), interleukin-3 (IL-3), SCF (stem cell factor) and GM-CSF; neutrophil activation induced by interleukin-8 (IL-8) or leukotriene B4; T cell proliferation in response to IL-2; and endothelial cell proliferation in response to acidic FGF (fibroblast growth factor).

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle and kidney mesengial cells; (2) suppresses up regulation of adhesion molecules as shown, for example, by blocking VCAM in endothelial cells of CD 18 in neutrophils; (3) inhibiting TNF, LPS and IL-1 induced metalloproteases (an inflammation model); (4) block LPS, TNF or IL-1 induced cellular activation (for prevention and treatment of septic shock); (5) suppress T cell and B cell activation by antigen of by cross-linking CD3 complex; (6) inhibit mast cell activation by IgE; and (7) suppress malignant phenotype in transformed cells and tumor cell lines.

The foregoing in vitro effects give rise to the following in vivo biologic effects, including, but not limited to, protection and treatment of endotoxic shock and sepsis induced by gram positive or gram negative bacteria, inhibition of tumor cell growth, stimulation of hematopoiesis following cytoreductive therapy, synergistic immunosuppression in preventing GVHD (graff versus host disease), and stimulation of hair grow through reversal of an apoptotic process. The inventive compounds are most potent when used to stimulate hematopoiesis, prevent and treat septic shock, treat acute and chronic inflammatory disease, treat or prevent an autoimmune disease, treat a fungal or yeast infection, and stimulate hair growth (when applied topically).

The inventive compounds also are useful as an adjuvant to inhibit toxic side effects of drugs whose side effects are mediated through the present second messenger pathway. These side effects include, for example, side effects of interleukin-2 (IL-2), renal side effects of cyclosporin A and FK506, and side effects of amphotericin B. It should be noted that the inventive compounds inhibit antigen-induced T cell activation, like cyclosporin or FK506, but, unlike cyclosporin or FK506, do not prevent generation of NK and LAK cells, do not suppress IL-2 release from T cells and do not suppress IL-8 release.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus βFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. PTX, by contrast in the same experiment, only inhibited PUMP-1 activity to 95% of its control levels which was not significant. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of interleukin-1 in Disease" (Dinarello and Wolff *N. Engl. J. Med.* 328, 106, Jan. 14, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, "the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension." "The therapeutic advantage of blocking the action of IL-1 resides in preventing its deleterious biologic effects without interfering with the production of molecules that have a role in homeostasis." The present inventive compounds address the need identified by Dinarello and Wolff by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ (PGE$_2$) and leukotriene $B_4$ (LTB$_4$) and IL-8, an inflammatory cytokine with neutrophil-chemoattractant and neutrophil-stimulating properties. Tissue concentrations of PGE2 and LTB4 correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, them is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. Activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl or 1-o-alkenyl acylglycerol (AAG) species. The inventive compounds exert their activity by inhibiting one or both enzymes at the inner leaflet of the plasma membrane. Therefore, appropriate in vitro models for drug activity is to measure inhibition of stimulation caused by a pro-inflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of diunsaturated PA, which is about <0.1% of total membrane lipid mass, is sufficient to activate PLD activity. This quantity of PA is similar to that endogenously synthesized by LPAAT. The PA-stimulated PLD acts upon PE, which should be localized to the inner leaflet of the cell membrane, which is enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e.,>30 min) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG on stimulation with mitogens, although the sources of DAG have differed between experimental systems. In nontransformed renal mesangial cells, IL-1 β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. The specific species of DAG that is stimulated by serum is dioleoyl and for PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds and PTX inhibit the conversion of the upregulated lysoPA to PA and subsequently block the phenotypic changes induced by PA/DAG in the membrane.

The ability of the inventive compounds and PTX to inhibit generation of unsaturated phospholipids is mirrored by the ability of PTX and other inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovims, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., *Nature* 330:662, 1987 and Hinshaw et al., *Circ. Shock* 30:279, 1990); cachexia (Dezube et at., *Lancet* 355:662, 1990), and adult respiratory distress syndrome (Miller et al., *Lancet* 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* 320:1585, 1989), chronic pulmonary inflammatory diseases such as silicosis and asbestosis (Piguet et at., *Nature* 344:245, 1990, and Bissonnette et at., *Inflammation* 13:329, 1989), and reperfusion injury (Vedder et al., *Proc. Natl. Acad. Sci. USA* 87:2643, 1990).

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells (in vivo or ex vivo) whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or Mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of Mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

The compounds of the invention can inhibit certain FGF (fibroblast growth factor) and PDGF (platelet derived growth factor) effects in vivo, such as inhibition of restenosis. For example, Ferns et al. (Science 253:1129, 1991) have shown that neointimal smooth muscle chemotaxis and angioplasty are inhibited in rats using a neutralizing antibody to PDGF. Also, Jawien et at. (*J. Clin Invest.* 89:507, 1992) have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et at., Science 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* 46:1066, 1990), metastatic melanoma cells (Yamanishi et at., *Cancer Res.* 52:5024, 1992), and glial tumors (Fleming et al., *Cancer Res.* 52:4550, 1992).

In Vitro Assays for Physiologic and Pharmacological Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microliter plate. Briefly, approximately $10^5$ test purified PBMC cells in 200 ml complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 mCi/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2 \times 10^5$ cells/well) and a stimulating agent, such as Con A, IL-1 (e.g., IL-1α) or IL-2 is added to the well. The cells are incubated for 4 days at 37° C. On the fourth day, the cells are pulsed with tritiated thymidine and cell proliferation determined. Inventive compounds are added at the time of stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (e.g., 2',7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 mg/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

One in vitro assay measures inhibition of the relevant enzymes lysophosphatidic acid acyltransferase (LPAAT) and phosphatidic acid phosphoryl hydrolase (PAPH). The assay involves incubation of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes, plasma membranes derived as described in Bursten et al. (J. Biol. Chem. 226:20732–20743, 1991), or detergent-solubilized microsomes; synaptosomes, and membranes or other cell preparations solubilized using, for example, NP-40, Miranal, SDS or other neutral detergents; and detergent-solubilized, recombinant, or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, Biochemistry 30:6195–6203, 1991. A Rainin® mu-Porasil column is used with a 3:4 hexane:propanol organic carder and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

Some of the inventive compounds are effective for inhibiting yeast cell growth. This effect can be assayed by measuring growth of the yeast strain *Saccharomyces cervisiae*. A control yeast stain *Saccharomyces cervisiae* (BIO 101, Inc.) is grown overnight in YEPD broth at 30° C. A one to hundred dilution of the yeast culture is made with fresh YEPD broth. 100 µl Aliquots of the diluted culture are distributed into 96-wells titer plates. 100 µl Aliquots of drug is diluted in YEPD broth were then added to the wells. The titer plates are incubated at room temperature with continuous shaking. The cell density of the individual cultures are determined using a microplate reader with a A630 filter. The A630 of the individual yeast cultures are compared to control samples without adding drug. This assay is predictive of direct antimicrobial, particularly yeast and fungal, activity of the drugs studied.

A serotonin release assay is utilized to study the utility of the inventive compounds for treatment of asthma and allergy. Some of the inventive compounds are particularly active for asthma and allergy indications. This assay measures mast cell degranulation, which is an early phase reaction to allergen challenge. Mast cells grown in tissue culture are first loaded with $^3$H serotonin, which is incorporated into the granules in the cells. The mast cells are sensitized with antigen specific monoclonal IgE, and then triggered to degranulate with the specific antigen (dinitorphenol bound to BSA (DNP)). When the cells degranulate, $^3$H Serotonin is released into the medium, and can be measured directly. The ability of the inventive compounds to inhibit the degranulation response is determined by the decrease in $^3$H Serotonin released in the presence of drug and is represented as % INHIBITION. The IC50 of any given compound is determined by the ability of that compound to inhibit degranulation by 50%.

Specifically, the serotonin release assay seeds $2 \times 10^5$ cells in 0.5 ml medium in duplicate for spontaneous release, IgE+DNP, IgE+DNP+EtOH (vehicle control), and inventive compounds. One µCi[$^3$H]-Serotonin/ml (i.e., 0.5 µCi/well) (NEN Research Products, cat. #NET-398 Hydroxytryptamine Binoxalate, 5-[1,2-$^3$H(N)]-(Serotonin Binoxalate, [1,2-$^3$H(N)]-)) and 1 µl/ml IgE is added. The cells are incubated for 18 hours at 37° C. in 5% $CO_2$, washed twice with 0.5 ml Isotonic Buffer (25 mM disodium PIPES pH 7.1,100 mM NaCl, 5 mM KCl, 5 mM glucose, 0.4 mM $MgCl_2$, 1mM $CaCl_2$, 0.1% BSA), and sterile filtered. 250 µl Isotonic Buffer is added per well and the plates are equilibrated in an incubator for about 10 min. Drug is added and cells are activated with 40 ng/ml DNP-BSA (1 mg/ml Diluted 1:200 in Isotonic Buffer) for 45 minutes using 2 µl/250 µl. Spontaneous release is determined in incubated cells with 250 µl Isotonic Buffer for 45 minutes and the reaction is stopped by removing supernatant and centrifuging at ~4000 rpm in microfuge for 15 seconds to remove any detached cells. Released radiolableled serotonin is counted. To determine amount of $^3$H-serotonin incorporated into the cells, (a) remove Isotonic Buffer and lyse cells by adding 250 µl 1% Triton-X100 in PBS, (b) add to 5 ml scintillation fluid, (c) wash 2× with Triton/PBS, and (d) add washes to scintillation tube. Percent serotonin release is calculated by dividing the amount of released serotonin by the sum of incorporated plus released serotonin and correcting for spontaneous released serotonin. Compound inhibition is calculated by dividing the percent serotonin release in the presence of a compound by the percent serotonin release in the absence of the compound.

There are a series of in vitro assays that can be used to measure immunosuppressive activity of a particular compound. These assays are a predictive model for treatment or prevention of autoimmune diseases, such as diabetes, lupus, arthritis, and the like. A first assay measures immunosuppressive activity of a drug at the B cell level. Spleens from adult mice contain immature B cells that express surface IgM. Cross-linking the surface IgM with an antimu antibody results in B cell proliferation. Additionally, this activation results in an increased expression of interleukin-4 receptors(IL-4R) on the surface of such cells. IL-4 acts as a growth factor for B cells and will increase the amount of proliferation induced by anti-mu. In the first assay, a mixture of anti-mu and murine IL-4 is added to murine splenocytes to cause their proliferation. Mice spleens are obtained from adult mice and a single cell suspension is prepared in RPMI 1640 medium supplemented with 10% FCS. Cells (200,000) are plated into flat-bottomed wells and pre-incubated for 1–2 hrs with various concentrations of drug or PBS if it is a control well. A mixture of anti-mu and murine is added to the wells at a final concentration of 5 mg/ml anti-mu and 12.5 ng/ml IL-4 and plates are incubated for three days. Proliferation is determined on the third day with a pulse of tritiated thymidine. The IC50 concentration of a particular drug is the concentration of drug that results in a 50% inhibition of the proliferation obtained from the positive control.

A second immune suppression assay measures a T cell component to the immune reaction. Lymph nodes contain a mixture of cells including T cells, B cells and macrophages. Although the proliferating cells in this assay are T cells, the response is also dependent upon an antigen presenting cell such as a macrophage as well as an elaboration of various immunoregulatory cytokines. Murine T cells will proliferate in vitro in response to a soluble o protein antigen if they are first primed with the antigen in vivo. In vivo priming involves emulsifying the antigen (chicken ovalbumin or OVA) in complete Freunds adjuvant and injecting 50 mg of OVA into both hind footpads of adult Balb/c mice. Fourteen days later the draining lymph nodes (popliteal) are removed and a single cell suspension is prepared in RPMI 1640 supplemented with 10% fetal calf serum. The lymph node cells (200,000) are plated into flat-bottom wells and OVA (200 mg/ml) and/or drug is added to appropriate wells and incubated for 5 days. Proliferation is determined and IC50's calculated as above.

A third assay measures an ability of an inventive compound to inhibit IL-2-induced proliferation of murine thymocytes. Thymus glands are obtained from 4–6 week old mice and plated as a single cell suspension into flat bottomed wells in RPMI 1640 medium supplemented with 10% fetal calf serum. The inventive compounds are added to appropriate wells and the cells are incubated for 1–2 hrs. Concanavilin A (ConA, 0.25 mg/ml) and IL-1 (20 ng/ml) are added and the plates are incubated for 4 days. Cell proliferation is determined as above.

Compounds of the Invention

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of a class of olefin-containing long chain substituted compounds, preferably heterocyclic compounds. The inventive compounds are effective in modulating cellular response to external or in situ primary stimuli, as well as to specific modes of administration of such compounds in effective amounts.

The inventive compounds comprise compounds and pharmaceutical compositions having the formula:

R—(core moiety), wherein R is a straight chain hydrocarbon having at least one double bond and a carbon chain length of from about 6 to about 18 carbon atoms, wherein multiple double bonds are separated from each other by at least three carbon atoms, wherein the closest double bond to the core moiety is at least five carbon atoms from the core moiety, and wherein the hydrocarbon chain may be substituted by a hydroxyl, halo, keto or dimethylanimo group and/or interrupted by an oxygen atom. Preferably, each double bond (with the exception of a terminal olefin) is in a cis configuration.

Preferably, the core moiety has from one to three, five to six membered ring structures in a predominantly planar structure. There can be from one to about three R substituents on each core moiety. Preferably, the olefin substituent (R) is bonded to a ring nitrogen if one exists. For example, the core moiety is selected from the group consisting of xanthine, halogen-substituted xanthines, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, 1-methyl-2,4(1H,3H)-quinazolinedione(1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4,3-d]pyrimidine, 5-substituted uracils, 6-substituted uracils, 1-methylpyrrolo[2,3-d]pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4(3H)-one, Most preferably, the heterocyclic core is a xanthine. The core moiety can also include a non-cyclic group. Examples of non-cyclic core groups include open chain analogs of glutarimide, carboxilic acid, a hydroxyl group, sulfone, sulfonate, and the like.

The present invention further provides a pharmaceutical composition comprising an inventive compound and a pharmaceutically acceptable excipient, wherein the pharmaceutical composition is formulated for oral, parenteral or topical administration to a patient.

The present invention further provides a method for treating an individual having a variety of diseases, wherein the disease is characterized by or can be treated by inhibiting an immune response or a cellular response to external or in situ primary stimuli, wherein the cellular response is mediated through a specific phospholipid-based second messenger acting adjacent to the inner leaflet of the cell membrane of a cell. The second messenger pathway is activated in response to various noxious or proliferative stimuli characteristic of a variety of disease states and the biochemistry of this second messenger pathway is described herein. More specifically, the invention is directed to methods that treat or prevent clinical symptoms of various disease states or reduce toxicity's of other treatments by inhibiting cellular signaling through the second messenger pathway described herein. The disease states or treatment-induced toxicity's are selected from the group consisting of proliferation of tumor cells in response to an activated oncogene; hematocytopenia caused by cytoreductive therapies; autoimmune diseases caused by a T-cell response or a B-cell response and antibody production; septic shock; resistance of mesenchymal cells to tumor necrosis factor (TNF); proliferation of smooth muscle cells endothelial cells, fibroblasts and other cell types in response to growth factors, such as PDGF-AA, BB, FGF, EGF, etc. (i.e., atherosclerosis, restenosis, stroke, and coronary artery disease); human immunodeficiency virus infection (AIDS and AIDS related complex); proliferation of kidney mesangial cells in response to IL-1, Mip-1α, PDGF or FGF; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drug or radiation); enhancing antitumor effects of nonalkylating antitumor agents; allergies in response to inflammatory stimuli (e.g., TNF, IL-1 and the like) characterized by production of cell surface metalloproteases or by degranulation of mast cells and basophils in response to IgE; bone diseases caused by overproduction of osteoclast-activating factor (OAF) by osteoclasts, CNS diseases caused by reduced signal transduction of the neurotransmitters epinephrine and acetylcholine, and combinations thereof. The inventive compounds are also useful as antimicrobial agents to directly treat fungal or yeast infections and to indirectly treat bacterial or viral infections through an immune stimulation and pro-hematopoietic effect.

The present invention further provides a pharmaceutical composition comprising an inventive compound and a pharmaceutically acceptable excipient, wherein the pharmaceutical composition is formulated for oral, parenteral or topical administration to a patient.

The present invention further comprises a pharmaceutical composition comprising one or a plurality of inventive compounds and a pharmaceutically acceptable carrier or excipient. The individuals to be treated with an inventive compound or inventive pharmaceutical composition may either be contacted with the compound of the invention in vitro culture, in an extracorporeal treatment, or by administering (oral, parenteral or topical) the compound of the invention or pharmaceutical composition to a subject whose cells are to be treated.

Illustrative compounds of the invention include both R and S enantiomers and racemic mixtures and cis and trans isomers and mixtures thereof of the following compounds:

TABLE 1

| | |
|---|---|
| CT1508 | 1-(6-cis-nonenyl)-3,7-dimethylxanthine |
| CT1524 | 1-(cis,cis-9,12-octadecadienyl)-3,7-dimethylxanthine |
| CT1531 | 1-(2-propenyl)-3,7-dimethylxanthine |
| CT1534 | 1-(6-heptenyl)-3,7-dimethylxanthine |
| CT1535 | 1-(7-octenyl)-3,7-dimethylxanthine |
| CT1539 | 1-(5-hexenyl)-3,7-dimethylxanthine |
| CT1550 | 1-(8-nonenyl)-3,7-dimethylxanthine |
| CT1563 | 1-(9,10-decenyl)-3,7-dimethylxanthine |
| CT1575 | 1-(4-pentenyl)-3,7-dimethylxanthine |
| CT1581 | 1-(4-hexenyl)-3,7-dimethylxanthine |
| CT1569R | 1-(3-(R)-methyl-7-methyloct-6-enyl)-3,7-dimethylxanthine |
| CT1569S | 1-(3-(S)-methyl-7-methyloct-6-enyl)-3,7-dimethylxanthine |
| CT2501 | 1-(10-undecenyl)-3,7-dimethylxanthine |
| CT2503 | 1-(3-butenyl)-3,7-dimethylxanthine |
| CT2508 | 1-(6-hydroxy-7-octenyl)-3,7-dimethylxanthine |
| CT2512 | 1-(6-trans-nonenyl)-3,7-dimethylxanthine |
| CT2516 | 1-(11-dodecenyl)-3,7-dimethylxanthine |
| CT2536R | 1-(4-(R)-methyl-8-methylnon-7-enyl)-3,7-dimethylxanthine |
| CT2536S | 1-(4-(S)-methyl-8-methylnon-7-enyl)-3,7-dimethylxanthine |
| CT2539 | 1-(9-octadecenyl)-3,7-dimethylxanthine |
| CT2544 | 1-(farnesyl)-3,7-dimethylxanthine |
| CT2545 | 1-(9-geranyl)-3,7-dimethylxanthine |
| CT2555 | 1-(12-tridecenyl)-3,7-dimethylxanthine |
| CT2560 | 1-(7-cis-decenyl)-3,7-dimethylxanthine |
| CT1405 | 1-(8-nonenyl)-3-methylxanthine |
| CT1406 | 1-(10-undecenyl)-3-methylxanthine |
| CT1438 | 1-(5-hexenyl)-3-methylxanthine |
| CT1442 | 1-(6-cis-nonenyl)-3-methylxanthine |
| CT1403 | 1-(10-undecenyl)-3-methyl-7-methylpivaloylxanthine |
| CT1411 | 1-(8-nonenyl)-3-methyl-7-methylpivaloylxanthine |
| CT1441 | 1-(5-hexenyl)-3-methyl-7-methylpivaloylxanthine |
| CT1101 | N(5-hexenyl)phthalimide |
| CT1102 | N(8-nonenyl)phthalimide |
| CT1107 | N(10-undecenyl)phthalimide |
| CT1203 | 1-(5-hexenyl)-3-methylbenzoyleneurea |
| CT1600 | N-(5-hexenyl)glutarimide |
| CT1604 | N-(8-nonenyl)glutarimide |
| CT1607 | N-(6-cis-nonenyl)glutarimide |
| CT1610 | N-(10-undecenyl)glutarimide |
| CT1700 | 2-(5-hexenyl)-1,3-cyclohexanedione |
| CT1800 | 1-methyl-3-(5-hexenyl)uracil |
| CT1814 | 3-(6-cis-nonenyl)1-methyluracil |
| CT1817 | 3-(8-nonenyl)1-methyluracil |
| CT1823 | 3-(10-undecenyl)1-methyluracil |
| CT1812 | 3-(5-hexenyl)-1-methyldihydrouracil |

TABLE 1-continued

| CT1819 | 3-(10-undecenyl)-1-methyldihydrouracil |
| CT1905 | 3-(5-hexenyl)-1-methylthymine |
| CT1916 | 3-(6-cis-nonenyl)-1-methylthymine |
| CT1917 | 3-(8-nonenyl)-1-methylthymine |
| CT1931 | 3-(10-undecenyl)-1-methylthymine |

Uses of the Inventive Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells (in vivo or ex vivo) whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or Mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of Mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Inventive compounds are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation. In addition, GVHD contributes to the death rate in allogeneic marrow recipients.

Deficiency of the female hormone 171β estradiol (E$_2$), caused by either menopause or removal of the ovaries, results in accelerated bone loss. As a consequence, bone mass declines after menopause and this decline is the major factor contributing to the high rate of disabling bone fractures in postmenopausal women. The pathogenic bone loss underlying this condition can be prevented by early estrogen replacement therapy, but the mechanism by which estrogens exert their bone sparing effects is unclear. Recent publications suggest that $E_2$ regulates the circuitry of cytokine action that controls bone remodeling. Bone remodeling is a process by which the catabolic effects (bone resorption) of one cell type of bone, osteoclasts, are balanced by the anabolic effects (bone formation) of a second cell type, osteoblasts. Normal bone remodeling proceeds in a highly regulated cycle in which osteoclasts adhere to bone and subsequently remove it by acidification and proteolytic digestion. Once osteoclasts leave the removal site, osteoblasts enter and secrete osteoid (a matrix of collagen and other proteins), which is calcified into new bone. Osteoclast-mediated resorption can be influenced by two processes, activation in which the resorptive function of mature osteoclasts is increased, and recruitment in which osteoclast progenitor cells are stimulated to yield more mature cells (generally derived from the same progenitor cells that give rise to circulating monocytes and tissue macrophages). Activation occurs when inducers of bone resorption, such as parathyroid hormone (PTH), IL-1 and TNF stimulate osteoblasts to secrete a specific set of cytokines (e.g., granulocyte macrophage colony stimulating factor (GM-CSF), macrophage colony stimulating factor (M-CSF), and interleukin-6 (IL-6)) to act directly on osteoclasts to cause bone resorption.

$E_2$ can regulate cytokines because PBM (peripheral blood monocytes) from either untreated premenopausal or estrogen- and progesterone-treated postmenopausal women with osteoporosis secreted less IL-1 than untreated postmenopausal women (nonosteoporotic and osteoporotic) (Pacifici et al., *Proc. Natl. Acad. Sci. USA* 84:4616, 1987). Therefore, the loss of $E_2$ that accompanies menopause allows PBM to secrete more IL-1 and $E_2$ inhibits IL-1 secretion. IL-1 is one of the most potent inducers of bone resorption in vitro and in vivo. IL-1 likely originates from macrophage-lineage cells within the bone. TNF, like IL-1, is a potent inducer of bone resorption, requires the presence of osteoblasts for its resorptive activity, and stimulates osteoblasts to secrete factors like GM-CSF and IL-6 to induce formation of osteoclasts from precursors. Thus, the loss of $E_2$ results in an increase in cytokines in the bone remodeling circuitry. Therefore, both IL-1 and TNF augment bone resorption, either directly or indirectly, and a drug that is both an IL-1 and TNF antagonist, should be effective for the treatment and prevention of bone loss and osteoporosis symptoms in postmenopausal women.

The inventive compounds inhibit cellular second messenger signaling, specifically through the IL-1 and TNF type I receptors and therefore function as IL-1 and TNF antagonists. Accordingly, the inventive compounds are useful for treating and preventing bone loss and osteoporosis.

Other indications for which it is useful to administer the compounds of the invention include the presence of a tumor burden, a hormone-related disorder, a neurological disorder, an autoimmune disease, inflammation, restenosis, coronary artery disease, atherosclerosis, hypertension, unwanted immune response, viral infection, nephritis, mucositis, and various allergic responses. Prevention of allergic responses include prevention of acute allergic response and thus moderation or prevention of rhinorrhea, sinus drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV 1, changes in vital capacity, and extensive mucus production.

Other suitable subjects for the administration of compounds of the invention, include patients being administered cytoreductive agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T-cells and B-cells, and patients who have neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention; in particular, dealkylation at the N7 position of the xanthine ring. For example, NIH3T3-D5C3 cells can be used to compare effects of an inventive compound alone or in combination with a P-450 inhibitor by comparing transformation phenotype control, incubation with an inventive compound alone, and coincubation of an inventive compound with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000 norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

Pharmaceutical Formulations

A suitable formulation will depend on the nature of the disorder to be treated, the nature of the medicament chosen and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely, but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory conditions, via parenteral administration, is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration, the dosage is suitably from about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral) Appropriate dosage forms include an aerosol or a metered dose inhaler, as prepared by conventional techniques. The daily dosage is suitably form about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

The invention is illustrated by the following examples which should not be regarded as limiting the invention in any way. In these examples PTX means pentoxifylline.

Example 1

This example illustrates the synthesis of 1-(6-cis-Nonenyl)-3,7-dimethylxanthine (CT1508). cis-6-Nonen-1-ol (3.00 g, 21.1 mmol) and methanesulfonyl chloride (1.6 ml, 2.4 g, 21 mmol) in $CH_2Cl_2$ (100 ml) at 0° C. was treated with triethylamine (4.4 ml, 3.2 g, 32 mmol). After 1 hr the ice bath was allowed to melt. After reaching room temperature, the reaction was poured into a separatory funnel containing water (50 ml) and $CH_2Cl_2$ (50 ml). The layers were separated and the aqueous layer washed with $CH_2Cl_2$ (2×50 ml). The organic layers were combined, dried ($Na_2SO_4$), and solvent removed to give 6-cis-nonene-1-methanesulfonate as a yellow oil (4.14 g, 18.8 mmol, 89% yield). The mesylate was used in the next step without further purification.

Theobromine (3.36 g, 18.8 mmol) and sodium hydride (451 mg, 18.8 mmol) in DMSO (40 ml) was stirred for 40 min, after which the mesylate (4.14 g, 18.8 mmol) was added. The reaction was stirred at 25° C. for 3 days, heated at 80° C. for 1 hr, then cooled. The reaction was poured into water (100 ml) and extracted with $CH_2Cl_2$ (3×60 ml). The organic layers were combined and washed with brine (2×50 ml) and dried ($Na_2SO_4$). The solvent was removed and the residue chromatographed (silica/ethyl acetate) to give CT1508 as a white solid (4.54 g, 79% yield).

Example 2

This example illustrates the synthesis of 3,7-Dimethyl-(cis,cis-9,12-octadecadienyl)xanthine (CT1524). Linoleyl alcohol (2.50 g, 9.4 mmol) and methanesulfonyl chloride (0.723 ml, 1.07 g, 9.4 mmol) in $CH_2Cl_2$ (50 ml) at 0° C. was treated with triethylamine (2.0 ml, 1.4 g, 14 mmol). After 1 hr the ice bath was allowed to melt. After reaching room temperature, the reaction was poured into a separatory funnel containing 1% HCl (80 ml) and $CH_2Cl_2$ (50 ml). The layers were separated and the aqueous layer extracted with $CH_2Cl_2$ (2×50 ml). The organic layers were combined, washed with saturated sodium bicarbonate, and dried ($Na_2SO_4$). The solvent was removed to give cis,cis-9,12-octadecadienyl-1-methanesulfonate as a yellow oil. The mesylate was used in the next step without further purification. Sodium theobromine (1.90 g, 9.4 mmol) and the mesylate was stirred at 25° C. in dimethylsulfoxide (30 ml) for 18 h. The reaction was poured into water (50 ml) and extracted with dichloromethane (3×50 ml). The organic layers were combined and washed with brine (2×50 ml) and dried over sodium sulfate. The solvent was removed and the residue recrystallized in ether to give CT1524 as a white solid (2.27 g, 59% yield).

Example 3

This example illustrates the synthesis of 1-(2-Propenyl)-3,7-dimethylxanthine (CT1531). Sodium hydride (72 mg, 3 mmol) was added to a solution of theobromine (540 mg, 3 mmol) in dimethylsulfoxide (20 ml) at room temperature. After the evolution of hydrogen gas ceased, 3-bromopropene (372 mg, 3.1 mmol) was addded. The mixture was agitated by swirling and then allowed to stand at room temperature for 15 hours. The solution was added to 0.1N HCl (200 ml) in a separatory funnel and then extracted with methylene chloride (2×100 ml). The organic solutions were dried over sodium sulfate and after removal of the salts by filtration the organic solvent was removed by evaporation to leave a white solid (280 mg, 42% yield).

Example 4

This example illustrates the synthesis of 1-(6-Heptenyl)-3,7-dimethylxanthine (CT1534). To a solution of 6-hepten-1-ol (6.00 g, 52.6 mmol) in dichloromethane (120 ml) at 0° C. was added methanesulfonyl chloride (6.07 g, 4.0 ml, 53.0 mmol) followed by triethylamine (7.79 g, 77.0 mmol). After stirring for 10 min at 0° C., the reaction was allowed to warm to 25° C. and stirred for 2 hr. The reaction was poured into water (100 ml) and extracted with dichloromethane (2×100 ml). The organic portions were combined, dried (magnesium sulfate), and evaporated to give the 7-methanesulfonyl-1-heptene as a yellow oil (9.30 g, 93%), which was used without further purification.

To a suspension of sodium theobromine (9.05 g, 50.0 mmol) in dimethylsulfoxide (90 ml) was added 7-methanesulfonyl-1-heptene (9.30 g, 48.2 mmol) and the reaction was stirred for 16 hr at 60° C. The mixture was then poured into water (100 ml) and extracted with ethyl acetate (3×100 ml). The organic portions were combined, dried, and evaporated to give an orange solid. Chromatography (silica, ethyl acetate/hexane) gave CT1534 as a white solid (6.50 g, 47%).

Example 5

This example illustrates the synthesis of 1-(7-Octenyl)-3,7-methylxanthine (CT1535). To a suspension of sodium hydride (580 mg, 24.2 mmol) in dimethylsulfoxide (100 ml) was added theobromine (3.96 g, 22.0 mmol). After 30 min, 8-bromo-1-octene (3.96 g, 22 mmol) was added and the reaction was stirred for 16 hr at 25° C. The mixture was then poured into 200 ml of water and extracted with dichloromethane (3×50 ml). The organic portions were combined, washed with brine (50 ml), dried (sodium sulfate), and evaporated to give CT1535 as a thick white oil which solidified upon standing (6.22 g, 97%).

Example 6

This example illustrates the synthesis of 1-(5-Hexenyl)-3,7-dimethylxanthine (CT1539). To a mixture of bromohexene (10.7 g, 66 mmol) (Aldrich) and sodium hydride (1.58 g, 66 mmol) in dimethylsulfoxide (100 ml) was added theobromine (11.9 g, 66 mmol) (Sigma) and stirred for 43 hr. The solution was treated with water (200 ml) and then extracted with dichloromethane (3×80 ml). The combined extracts were washed with water (3×100 ml), dried over magnesium sulfate, and then the solvent was evaporated under vacuum to give CT1539 (17 g, 65 mmol, 98% yield) as a white powder.

Example 7

This example illustrates the synthesis of 1-(9-Decenyl)-3,7-dimethylxanthine (CT1563). To a solution of 9-decene-1-ol (Aldrich, 3.00 g, 19.2 mmol) in dichloromethane (100 ml) at 0° C. was added mesyl chloride (2.20 g, 1.5 ml, 19.2 mmol) followed by triethylamine (2.91 g, 28.8 mmol) After stirring for 15 min at 0° C., the reaction was allowed to warm to room temp. After 2 hr, the reaction was poured into 100 ml water and extracted with dichloromethane (3×60 ml). The organic portions were combined, dried (sodium sulfate), and evaporated to give the mesylate as a yellow oil (4.52 g, 100%). The mesylate was used without further purification.

To a suspension of sodium hydride (461 mg, 19.2 mmol) in dimethylsulfoxide (30 ml) was added theobromine (3.45 g, 19.2 mmol). After 15 min the 9-decene-1-mesylate (2.25 g, 11 mmol) was added and the reaction stirred 18 hr at 25° C., then at 100° C. for 40 min. The mixture was then poured into 100 ml water and extracted with dichloromethane (3×50 ml). The organic portions were combined, washed with brine (60 ml), dried (magnesium sulfate), and evaporated to give a white solid. Recrystallization in ether gave CT1563 as a colorless oil (3.40 g, 56% yield).

Example 8

This example illustrates the synthesis of 1-(4-pentenyl)-3,7-dimethylxanthine (CT1575). Sodium hydride (95%) (1.38 g, 55 mmol) was added to a solution of theobromine (9.0 g, 50 mmol) in dimethylsulfoxide (300 ml). After 20 min of stirring, 1-bromo-4-pentene (7.45 g, 50 mmol) was added. After 16 hr of stirring at room temperature, the reaction was poured into a separatory funnel containing 1 L of water and extracted with dichloromethane (5×200 ml). The organic extracts were combined, washed with water (100 ml) and brine (100 ml), dried over anhydrous magnesium sulfate and concentrated under reduced pressure. The crude product obtained was further purified by flash chromatography over silica gel (eluant: 20% petroleum ether/ethyl acetate) to give the olefin CT1575 (9.67 g 92% yield).

Example 9

This example illustrates the synthesis of 1-(trans-4-Hexenyl)-3,7-dimethylxanthine (CT1581). To a solution of trans-4-hexen-1-ol (1.22 g, 12.2 mmol) and methanesulfonyl chloride (1.04 ml, 13.4 mmol) in dichloromethane (15 ml), cooled in an ice bath, was added triethylamine (2.55 ml, 18.3 mmol) dropwise. After 5 min, the cooling bath was removed and the mixture was stirred for 45 min. The mixture was treated with saturated aqueous sodium bicarbonate solution (25 ml) and then the layers were separated and the aqueous layer was extracted with dichloromethane (20 ml). The combined organic layers were dried over magnesium sulfate and volatiles were evaporated under vacuum to give the mesylate.

To the mixture of theobromine (2.16 g, 12.0 mmol) and sodium hydride (288 mg, 12.0 mmol) in dimethylsulfoxide (40 ml) was added a solution of this mesylate in dimethylsulfoxide (10 ml). After stirring for 90 hr, the mixture was treated with water (70 ml) o and extracted with ether (30×50 ml). The combined extracts were washed with water (50 ml), dried over magnesium sulfate, and then the solvent was evaporated under vacuum. The residue was purified by flash chromatography (22 g of silica gel) eluting with ethyl acetate (500 ml) to give CT1581 (2.1 g, 8.0 mmol, 67% yield) as white crystals.

Example 10

This example illustrates the synthesis of 1-(3-(R)-methyl-7-methyloct-6-enyl)-3,7-dimethylxanthine (CT1596R). Sodium hydride (95%) (631 mg, 25 mmol) was added to a solution of theobromine (4.14 g, 23 mmol) in DMSO (75 ml). After 20 min of stirring, (R)(−) Citronellyl bromide (5.0 g, 22.8 mmol) was added. After 16 hr of stirring at room temperature, the reaction was poured into a separatory funnel containing 500 ml of water and extracted with dichloromethane (3×100 ml). The organic extracts were combined, washed with water (100 ml) and brine (100 ml), dried over anhydrous MgSO4 and concentrated under reduced pressure. The crude product obtained was further purified by flash chromatography over silica gel (eluant: 30% petroleum ether/ethyl acetate) to give the olefin CT1596R as a yellowish oil (5.9 g 81.5% yield).

Example 11

This example illustrates the synthesis of 1-(3-(S)-methyl-7-methyloct-6-enyl)-3,7-dimethylxanthine (CT1596S). Sodium hydride (95%) (631 mg, 25 mmol) was added to a solution of theobromine (4.14 g, 23 mmol) in DMSO (75 ml). After 20 min of stirring, (R)(−) Citronellyl bromide (5.0 g, 22.8 mmol) was added. After 16 hr of stirring at room temperature, the reaction was poured into a separatory funnel containing 500 ml water and extracted with dichloromethane (3×100 ml). The organic portions were combined, washed with water (100 ml) and brine (100 ml), dried over anhydrous $MgSO_4$ and concentrated under reduced pressure. The crude product obtained was further purified by flash chromatography over silica gel (eluant: 30% petroleum ether/ethyl acetate) to give the olefin CT1596S as a yellow oil (5.78g 80% yield).

Example 12

This example illustrates the synthesis of 1-(6-trans-nonenyl)-3,7-dimethylxanthine (CT2512). A mixture of 6-cis-nonen-1-ol (TCI, 990 mg, 7.0 mmol) and thiophenol (60 mg) was heated at 105°–110° C. under argon for 4 hr to give 6-nonen-1-ol (872 mg, 88% yield) with a 4:1 ratio of trans:cis isomers. Without further purification, the olefin mixture was stirred with methanesulfonyl chloride (694 mg, 6.1 mmol) in dichloromethane (20 ml) at 0° C. Triethylamine (925 mg, 9.2 mg) was added dropwise and stirring was continued for 1 hr. The reaction mixture was added to an aqueous saturated solution of sodium bicarbonate (10 ml) and the layers were separated. The aqueous layer was extracted with dichloromethane (2×15 ml). The combined organic layers were washed with a 5% solution of hydrogen chloride (10 ml), water (10 ml), and an aqueous saturated solution of sodium chloride (10 ml), then dried over sodium sulfate. The solvent was removed under vacuum to give the mesylate, which was used in the next step without purification.

A mixture of the mesylate, sodium theobromine (1.21 g, 6.0 mmol) was stirred in dimethylsulfoxide (10 ml) for 24 hr. The reaction mixture was poured into water (10 ml) and extracted with dichloromethane (3×25 ml). The combined organic extracts were washed with water (15 ml) and aqueous saturated salt solution (15 ml). After removing the solvent under vacuum, the residue was chromatographed (silica/ethyl acetate) to give 1-(6-trans-noneyl)-3,7-dimethylxanthine CT2512 (827 mg, 67% yield), 20% contaminated with the cis isomer.

Example 13

This example illustrates the synthesis of 1-(11-Dodecenyl)-3,7-dimethylxanthine (CT2516). To a suspension of magnesium (6.4 g, 265 mmol) and a crystal of iodine in tetrahydrofuran (40 ml) was added 10-undecenyl bromide (12.25 g, 53.0 mmol) in tetrahydrofuran (30 ml) over 30 min and the reaction stirred for a further 30 min after the addition was complete. The solution was added via a canula over 5 min to a suspension of paraformaldehyde (1.80 g, 60.0 mmol) in tetrahydrofuran (40 ml) and stirred at 25° C. for 16 hr. Saturated ammonium chloride (80 ml) was added and extracted with diethyl ether (2×100 ml). The combined organic extracts were dried (magnesium sulfate) and evaporated to give a residue which was distilled at 2 mm Hg to afford 11-dodecenyl alcohol as a clear liquid (6.53 g, 67%, b.p. 105°–107° C.).

To a solution of 11-dodecen-1-ol (5.5 g, 29.9 mmol) in dichloromethane (70 ml) at 0° C. was added methanesulfonyl chloride (3.55 g, 2.40 ml, 31.0 mmol) followed by triethylamine (4.38 g, 46.0 mmol). After stirring for 10 min at 0° C., the reaction was allowed to warm to 25° C. and stirred for 2 hr. The reaction was poured into water (60 ml), separated and washed with dichloromethane (50 ml). The organic portions were combined, dried (magnesium sulfate), and evaporated to give the 12-methanesulfonyl-1-dodecene as a yellow oil which was used without further purification.

To a suspension of sodium theobromine (6.00 g, 30.0 mmol) in dimethylsulfoxide (60 ml) was added 12-methanesulfonyl-1-dodecene and the reaction stirred for 16 hr at 60° C. The mixture was then poured into water (120 ml) and extracted with diethyl ether (2×100 ml). The organic portions were combined, dried (magnesium sulfate), and evaporated to give a cream solid. Recrystallisation from ethyl acetate/hexane 1:1 gave CT2516 as a white solid (6.97 g, 67%).

Example 14

This example illustrates the synthesis of 1-(4-(R)-Methyl-8-methylnon-7-enyl)-3,7-dimethylxanthine (CT2536R). To a suspension of magnesium (2.74 g, 140 mmol) and a crystal of iodine in tetrahydrofuran (15 ml) was added (R)-citronellyl bromide (5.0 g, 22.8 mmol) in tetrahydrofuran (10 ml) over 30 min and the reaction stirred for a further 30 min after the addition was complete. The solution was added via a canula over 5 min to a suspension of paraformaldehyde (1.80 g, 60.0 mmol) in tetrahydrofuran (15 ml) and stirred at 25° C. for 6 hr. Saturated ammonium chloride (40 ml) was added and extracted with diethyl ether (2×30 ml). The combined organic extracts were dried (magnesium sulfate) and evaporated to give 4-(R)-methyl-8-methylnon-7-enyl alcohol as a clear liquid (3.25 g, 84%).

To a solution of 4-(R)-methyl-8-methylnon-7-enyl alcohol (3.25 g, 19.1 mmol) in dichloromethane (50 ml) at 0° C. was added methanesulfonyl chloride (2.29 g, 20.0 mmol) followed by triethylamine (3.04 g, 30.0 mmol). After stirring for 10 min at 0° C., the reaction was allowed to warm to 25° C. and stirred for 3 hr. The reaction was poured into water (50 ml), separated and washed with dichloromethane (50 ml). The organic portions were combined, dried (magnesium sulfate), and evaporated to give the 1-methanesulfonyl-4-

(R)-methyl-8-methylnon-7-ene as a yellow oil which was used without further purification.

To a suspension of sodium theobromine (4.05 g, 20.0 mmol) in dimethylsulfoxide (50 ml) was added 1-methanesulfonyl-4-(R)-methyl-8-methylnon-7-ene and the reaction stirred for 16 hr at 60° C. The mixture was then poured into water (100 ml) and extracted with ethyl acetate (100 ml, 2×50 ml). The organic portions were combined, dried (magnesium sulfate), and evaporated to give a residue which was purified by column chromatography (ethyl acetate/hexane) CT2536R as a white solid (1.70 g, 28% yield).

Example 15

This example illustrates the synthesis of 1-(4-(S)-Methyl-8-methylnon-7-enyl)-3,7-dimethylxanthine (CT2536S). To a suspension of magnesium (2.74 g, 140 mmol) and a crystal of iodine in tetrahydrofuran (15 ml) was added (S)-citronellyl bromide (5.0 g, 22.8 mmol) in tetrahydrofuran (10 ml) over 30 min and the reaction stirred for a further 30 min after the addition was complete. The solution was added via a canula over 5 min to a suspension of paraformaldehyde (1.80 g, 60.0 mmol) in tetrahydrofuran (15 ml) and stirred at 25° C. for 6 hr. Saturated ammonium chloride (40 ml) was added and extracted with diethyl ether (2×30 ml). The combined organic extracts were dried (magnesium sulfate) and evaporated to give 4-(S)-methyl-8-methylnon-7-enyl alcohol as a clear liquid (3.25 g, 84%).

To a solution of 4-(S)-methyl-8-methylnon-7-enyl alcohol (3.25 g, 19.1 mmol) in dichloromethane (50 ml) at 0° C. was added methanesulfonyl chloride (2.29 g, 20.0 mmol) followed by triethylamine (3.04 g, 30.0 mmol) After stirring for 10 min at 0° C., the reaction was allowed to warm to 25° C. and stirred for 3 hr. The reaction was poured into water (50 ml), separated and washed with dichloromethane (50 ml). The organic portions were combined, dried (magnesium sulfate), and evaporated to give the 1-methanesulfonyl-4-(S)-methyl-8-methylnon-7-ene as a yellow oil which was used without further purification.

To a suspension of sodium theobromine (4.05 g, 20.0 mmol) in dimethylsulfoxide (50 ml) was added 1-methanesulfonyl-4-(S)-methyl-8-methylnon-7-ene and the reaction stirred for 16 hr at 60° C. The mixture was then poured into water (100 ml) and extracted with ethyl acetate (100 ml, 2×50 ml)). The organic portions were combined, dried (magnesium sulfate), and evaporated to give a residue which was purified by column chromatography (ethyl acetate/hexane) CT2536S as a white solid (1.83 g, 30% yield).

Example 16

This example illustrates the synthesis of 1-(9-Octadecenyl)-3,7-dimethylxanthine (CT2539) and 1-(9-Octadecenyl)-3,7-dimethylxanthine (CT2539). A preparation of 1-Bromo-9-octadecene triphenylphosphine (5.24 g; 20 mmol) was added in portions to a solution of oleyl alcohol (5.37 g; 20 mmol) and carbontetrabromide (6.63 g; 20 mmol) in 400 ml of dichloromethane and stirred for an hour at room temperature. The solvent was removed under reduced pressure and the residue was extracted with hexane (3×200 ml). Further purification was done by flash chromatography over silica gel using hexane as eluant (5.82 g 88% yield).

Sodium hydride (95%) (84 mg, 3.5 mmol) was added to a solution of theobromine (0.595 g, 3.2 mmol) in dimethylsulfoxide (15 ml). After 20 min of stirring, 1-bromo-9-octadecene (0.995 g, 3 mmol) was added. After 6hr of stirring at room temperature, the reaction mixture was warmed to 60° C. for 3 hr and then poured into a separatory funnel containing 50 ml of water and extracted with dichloromethane (5×40 ml). The organic extracts were combined, washed with water (50 ml) and brine (50 ml), dried over anhydrous magnesium sulfate and concentrated under reduced pressure. The crude product obtained was further purified by flash chromatography over silica gel (eluant: 30% acetone/petroleum ether) to give the olefin CT2539 (0.44 g 34% yield).

Example 17

This example illustrates the synthesis of 1-(Farnesyl)-3,7-dimethylxanthine (CT2544). Sodium hydride (95%) (0.28 g, 12 mmol) was added to a solution of theobromine (2.16 g, 12 mmol) in dimethylsulfoxide (50 ml). After 20 min of stirring, farnesyl bromide (2.85 g, 10 mmol) was added. After 6 hr of stirring at room temperature, the reaction mixture was warmed to 60° C. for 3 hr and then poured into a separatory funnel containing 150 ml of water and extracted with dichloromethane (5×75 ml). The organic extracts were combined, washed with water (50 ml) and brine (50 ml), dried over anhydrous magnesium sulfate and concentrated under reduced pressure. The crude product obtained was further purified by flash chromatography over silica gel (eluant: 30% acetone/petroleum ether) to give the olefin CT2544 (2.4 g 63.2% yield).

Example 18

This example illustrates the synthesis of 1-(Geranyl)-3,7-dimethylxanthine (CT2545). Sodium hydride (95%) (0.28 g, 12 mmol) was added to a solution of theobromine (2.16 g, 12 mmol) in dimethylsulfoxide (50 ml). After 20 min of stirring, geranyl bromide (2.17 g, 10 mmol) was added. After 6 hr of stirring at room temperature, the reaction mixture was warmed to 60° C. for 3 hr and then poured into a separatory funnel containing 150 ml of water and extracted with dichloromethane (5×75 ml). The organic extracts were combined, washed with water (50 ml) and brine (50 ml), dried over anhydrous magnesium sulfate and concentrated under reduced pressure. The crude product obtained was further purified by flash chromatography over silica gel (eluant: 30% acetone/petroleum ether) to give the olefin CT2545 (2.1 g 66.5% yield).

Example 19

This example illustrates the synthesis of 1-(12-Tridecenyl)-3,7-dimethylxanthine (CT2555). To a suspension of magnesium (4.12 g, 172 mmol) and a crystal of iodine in tetrahydrofuran (40 ml) was added 10-undecenyl bromide (8.00 g, 34.3 mmol) in tetrahydrofuran (30 ml) over 30 min and the reaction stirred for a further 30 min after the addition was complete. The solution was added via a canula over 5 min to a solution of ethylene oxide (2.65 g, 60.0 mmol) in tetrahydrofuran (30 ml) and stirred at 25° C. for 16 hr. Saturated ammonium chloride (100 ml) and 1M hydrogen chloride (200 ml) were added and extracted with diethyl ether (2×200 ml). The combined organic extracts were dried (magnesium sulfate) and evaporated to give a residue which was distilled at 1.5 mm Hg to afford 12-tridecenyl alcohol as a clear liquid (4.11 g, 61%, b.p. 98°–101° C.).

To a solution of 12-tridecen-1-ol (2.11 g, 10.7 mmol) and carbon tetrabromide (4.37 g, 13.1 mmol) in dichloromethane (15 ml) at 0° C. was added triphenyl phosphine (3.45 g, 13.1 mmol) in portions over 5 min. After stirring for 1.5 h at 25°

C. the solvent was evaporated and the residue extracted with hexane (3×30 ml), filtering off any solids. The solvent was evaporated to afford 12-tridecenyl bromide as a clear oil which was used without further purification.

To a suspension of sodium theobromine (2.22 g, 11.0 mmol) in dimethylsulfoxide (25 ml) was added 12-tridecenyl bromide and the reaction stirred for 16 hr at 60° C. The mixture was then poured into water (80 ml) and extracted with dichloromethane (3×50 ml). The combined organic portions were washed with water (3×100 ml), dried (magnesium sulfate), and evaporated to give a gummy residue. Purification by column chromatography (ethyl acetate/hexane) gave CT2555 as a whim solid (1.89 g, 50% yield).

Example 20

This example illustrates the synthesis of N-(5-Hexenyl)phthalimide (CT1101). 1-bromo-5-hexene (6.52 g, 40 mmol) was added to a suspension of potassium phthalimide (7.4 g; 40 mmol) in 50 ml of dimethyl sulfoxide and stirred overnight. After 12 hr of stirring at room temperature, the reaction was poured into a separatory funnel containing 300 ml of water and extracted with dichloromethane (5×200 ml). The organic extracts were combined, washed with water (100 ml) and brine (100 ml), dried over anhydrous magnesium sulfate and concentrated under reduced pressure. The crude product obtained was further purified by flash chromatography over silica gel (eluant: 10% acetone/hexane) to give the olefin CT1101 (9.2 g 100% yield).

Example 21

This example illustrates the synthesis of N-(8-Nonenyl)phthalimide (CT1102). 1-bromo-8-nonene (8.2 g, 40 mmol) was added to a suspension of potassium phthalimide (7.4 g, 40 mmol) in 50 ml of dimethyl sulfoxide and stirred overnight. After 12 hr of stirring at room temperature, the reaction was poured into a separatory funnel containing 300 ml of water and extracted with dichloromethane (5×200 ml). The organic extracts were combined, washed with water (100 ml) and brine (100 ml), dried over anhydrous magnesium sulfate and concentrated under reduced pressure. The crude product obtained was further purified by flash chromatography over silica gel (eluant: 10% acetone/hexane) to give the olefin CT1101 (7.6 g 70.4% yield).

Example 22

This example illustrates the synthesis of 1-(5-Hexenyl)-3-methylbenzoyleneurea (CT1203). A solution of dimethyl sulfoxide (50 ml), sodium hydride (0.17 g, 6.8 mmol) and 3-methylbenzoyleneurea (see below) (1.07 g, 6.1 mmol) was stirred under argon. After 10 min, to this slurry was added 1-hexenylbromide (0.82 ml, 6.8 mmol). After 14 hr, water (50 ml) was added to the dimethyl sulfoxide solution (heat evolution) and allowed to stir for 20 min. The aqueous dimethyl sulfoxide solution was extracted with dichloromethane (3×30 ml). The organic phases were combined and washed with water (3×50 ml). The solution was dried over sodium sulfate, filtered, and the solvent removed under vacuum. The residue yielded a white solid CT1203 (1.51 g, 96% yield).

This example also illustrates the synthesis of 3-Methylbenzoyleneurea used in this example. A solution of dimethyl sulfoxide (100 ml), sodium hydride (0.76 g, 30 mmol), and benzoyleneurea (4.86 g, 30 mmol) was stirred under argon for 10 min. To this slurry was added methyl iodide (1.87 ml, 30 mmol). After 14 hr, water (100 ml) was added to the dimethyl sulfoxide solution (heat evolution) and allowed to stir for 20 min. The aqueous dimethyl sulfoxide solution was extracted with dichloromethane (3×100 ml). A white precipitate was filtered and the dichloromethane phase was dried over sodium sulfate. The solution was filtered and the solvent removed under vacuum. The residue was recrystallized with hot dichloromethane to yield a white solid CT1201 (1.3 g, 25%).

Example 23

This example illustrates the synthesis of 3-Methyl-1-(8-nonenyl)xanthine (CT1405). 3-Methyl-7-methylpivaloyl-1-(8-nonenyl xanthine CT1411 (see below) (250 mg, 0.6 mmol) was dissolved in methanol (4 ml) and treated with a solution of sodium methoxide (prepared from 14 mg of sodium in 3 ml methanol). After stirring at room temperature for 3 hr, the reaction was poured into 10 ml water and extracted with dichloromethane/15% methanol (4×40 ml). The organic portions were combined and washed with brine (10 ml), then dried (sodium sulfate) and the solvent removed. Chromatography of the residue (silica, dichloromethane/8% methanol) followed by recrystallization (dichloromethane/5% ethanol) gave CT1405 as a white solid (35 mg, 20% yield).

This example also illustrates the synthesis of 3-Methyl-7-methylpivaloyl-1-(8-nonenyl)xanthine (CT1411). 3-Methyl-7-(methylpivalyl)xanthine CT1404 (see below) (2.14g, 7.6 mmol) and sodium hydride (183 mg, 7.6 mmol) in dimethyl sulfoxide (30 ml) was stirred for 15 min, after which 9-bromo-1-nonene (1.56 g, 7.6 mmol) was added. After stirring at room temperature for 2 days, the reaction was poured into 50 ml water and extracted with dichloromethane (3×50 ml). The organic portions were combined and washed with water (2×20 ml) and brine (30 ml). The solvent was removed to give a thick oil. Chromatography (silica, EtOAc/20% hexane) of this residue yielded CT1411 as a white solid (1.46 g, 48%).

This example also illustrates the synthesis of 3-Methyl-7-(methylpivaloyl)xanthine (CT1404). A mixture of 3-methylxanthine (Aldrich, 1.00 g, 6.0 mmol) and sodium hydride (145 mg, 6.0 mmol) in dimethyl sulfoxide (20 ml) was stirred until homogeneous (0.5 hr). Chloromethylpivalate (865 ml, 904 rag, 6.0 mmol) was added and the reaction was stirred 18 hr. The reaction was poured into 70 ml water, followed by extraction with 25% ethanol/dichloromethane (4×60 ml). The combined organic extracts were dried (sodium sulfate), then rotovapped to a volume of 40 ml. This solution was cooled in ice water, whereupon a thick white precipitate formed. The solid was filtered off under suction and dried under vacuum to give the pivalate CT1404 (1.43 g, 5.4 mmol, 90% yield).

Example 24

This example illustrates the synthesis of 1-(10-undecenyl)-3-methylxanthine (CT1406). Sodium methoxide (25 mg, 0.463 mmol) was added to a solution of 1-(10-undecenyl)-7-pivaloyl-3-methylxanthine (CT1403, see below) (175 mg, 0.463 mmol) in 5 ml of methanol and stirred for 6 hr at room temperature. The reaction mixture was quenched with saturated ammonium chloride solution (5 ml) and extracted with 20% ethanol/dichloromethane (5×50 ml). The organic extracts were combined, washed with brine (30 ml), dried over anhydrous magnesium sulfate and concentrated under reduced pressure. The crude product obtained was further purified by flash chromatography over silica gel (eluant: ethyl acetate) to give the olefin CT1406 (117 mg, 91.4% yield).

This example also illustrates the synthesis of 1-(10-undecenyl)-7-methylpivaloyl-3-methylxanthine (CT1403). Sodium hydride (76.8 mg, 3.2 mmol) was added to a solution of 3-methyl-7-pivaloylxanthine CT1404 (see example 23 above) (0.84 g, 3 mmol) and 11-bromoundec-10-ene (0.745 g; 3.2 mmol) in 15 ml of dimethyl sulfoxide and stirred overnight. After 12 hr of stirring at room temperature, the reaction was poured into a separatory funnel containing 30 ml of water and extracted with dichloromethane (5×50 ml). The organic extracts were combined, washed with water (30 ml) and brine (30 ml), dried over anhydrous magnesium sulfate and concentrated under reduced pressure. The crude product obtained was further purified by flash chromatography over silica gel (eluant: 50% hexane/ethyl acetate) to give the olefin CT1403 (1.05 g, 73.8% yield).

Example 25

This example illustrates the synthesis of 1-Methyl-3-(5-hexenyl)xanthine (CT1438). To 1-(5-Hexenyl)-3-methyl-7-(methylpivaloyl)xanthine CT1441 (see below) (82 mg, 0.20 mmol) in methanol (2 ml) was added a solution of sodium methoxide (prepared from 6 mg sodium and 1 ml methanol). After 10 min, the reaction was poured into 30 ml water and extracted with dichloromethane/20% ethanol (5×30 ml). Organic portions combined, dried (magnesium sulfate), and the solvent removed to give CT1438 (43 mg, 87%).

This example also illustrates the synthesis of 1-(5-Hexenyl)-3-methyl-7-(methylpivaloyl)xanthine (CT1441) Sodium hydride (86 mg, 3.6 mmol) was added to a stirring solution of 3-methyl-7-(methylpivaloyl)xanthine CT1404 (see example 23 above) (1.00 g, 3.6 mmol) in dimethyl sulfoxide (25 ml). After 15 min, 6-bromo-1-hexene (589 mg, 3.6 mmol) was added and the mixture was stirred for 72 hr. The reaction was then poured into 70 ml water and extracted with dichloromethane (2×100 ml) and with 20% ethanol/dichloromethane (1×100 ml). The organic layers were combined, washed with brine (50 ml) and dried (magnesium sulfate). The solvent was evaporated to give a thick oil which was chromatographed (silica, ethyl acetate) to give CT1441 (870 mg, 67% yield).

Example 26

This example illustrates the synthesis of 3-Methyl-1-(6-cis-nonenyl)xanthine (CT1442). cis-6-Nonen-1-ol (TCI, 3.00 g, 21.1 mmol) and methanesulfonyl chloride (1.6 ml, 2.4 g, 21 mmol) in dichloromethane (100 ml) at 0° C. was treated with triethylamine (4.4 ml, 3.2 g, 32 mmol). After 1 hr the ice bath was allowed to melt. After reaching room temperature, the reaction was poured into a separatory funnel containing water (50 ml) and dichloromethane (50 ml). The layers were separated and the aqueous layer washed with dichloromethane (2×50 ml). The organic layers were combined, dried (sodium sulfate), and solvent removed to give 6-cis-nonene-1-methanesulfonate as a yellow oil (4.14 g, 18.8 mmol, 89% yield). The mesylate was used in the next step without further purification.

Example 27

This example illustrates the synthesis of 1-(5-Hexenyl)glutarimide (CT-1600). Sodium hydride (425 mg, 17.7 mmol) was added to a solution of glutarimide (2.00 g, 7.7 mmol) in dimethyl sulfoxide (40 ml). After 20 min of stirring, 6-bromo-1-hexene (2.90 g, 17.7 mmol) was added. After 20 hr of stirring, the reaction was poured into a separatory funnel containing 100 ml water and extracted with dichlormethane (4×50 ml). The organic portions were combined, washed with water (50 ml) and brine (50 ml) and dried to give the olefin CT1600 as a colorless oil (2.92 g, 85% yield).

Example 28

This example illustrates the synthesis of 1-(8-Nonenyl)glutarimide (CT1604). Sodium hydride (1.02 g, 44 mmol) was added to a solution of glutarimide (5.00 g, 44 mmol) in dimethyl sulfoxide (150 ml). After 20 min of stirring, 9-bromo-1-nonene (9.02 g, 44 mmol) was added. After 16 hr of stirring at room temperature, the reaction was poured into a separatory funnel containing 100 ml water and extracted with dichlormethane (3×70 ml). The organic portions were combined, washed with water (2×40 ml) and brine (50 ml) and dried to give the olefin CT1604 as a colorless oil (10.09 g, 97% yield).

Example 29

This example illustrates the synthesis of 1-(6-cis-Nonenyl)glutarimide (CT1607). Sodium hydride (95%) (120 mg, 5 mmol) was added to a solution of glutarimide (452 mg, 4 mmol) in dimethyl sulfoxide (10 ml). After 20 min of stirring, 6-cis-nonenyl mesylate (885 mg, 4 mmol) was added and stirred for 12 hr at room temperature. The reaction was warmed to 70°–80° C. and stirred for 4 hr. The reaction mixture was then poured into a separatory funnel containing 100 ml of water and extracted with dichlormethane (5×50 ml). The organic extracts were combined, washed with water (50 ml) and brine (50 ml), dried over anhydrous magnesium sulfate and concentrated under reduced pressure. The crude product obtained was further purified by flash chromatography over silica gel (eluant: 20% ethyl acetate/hexane) to give the olefin CT1607 (120 mg 12.6% yield).

Example 30

This example illustrates the synthesis of 3-Hexenyl-1-methyluracil (CT1800). Sodium hydride (86 mg, 3.6 mmol) was added to a stirring solution of 1-methyluracil (500 mg, 4 mmol) in dimethyl sulfoxide (25 ml). After 15 min, 6-bromo-1-hexene (647 mg, 4 mmol) was added and the mixture stirred for 20 hr. The reaction was then poured into 50 ml water and extracted with 20% ethanol/dichloromethane (3×50 ml). The organic layers were combined, washed with brine (20 ml) and dried (sodium sulfate). The solvent was evaporated to give a residue which was chromatographed (silica, ethyl acetate) to give CT1800 (598 mg, 72% yield).

Example 31

This example illustrates the synthesis of 3-(6-cis-Nonenyl)-1-methyluracil (CT1814). Sodium hydride (95%) (120 mg, 5 mmol) was added to a solution of 1-methyl uracil (504.4 mg, 4 mmol) in dimethyl sulfoxide (10 ml). After 20 min of stirring, 6-cis-nonenyl mesylate (885 mg, 4 mmol) was added and stirred for 12 hr at room temperature. The reaction was warmed to 70°–80° C. and stirred for 4 hr. The reaction mixture was then poured into a separatory funnel containing 100 ml of water and extracted with dichloromethane (5×50 ml). The organic extracts were combined, washed with water (50 ml) and brine (50 ml), dried over anhydrous magnesium sulfate and concentrated under reduced pressure. The crude product obtained was further purified by flash chromatography over silica gel (eluant: 40% ethyl acetate/pentane) to give the olefin CT1814 (401 mg 40.1% yield).

Example 32

This example illustrates the synthesis of 1-Methyl-3-(8, 9-nonenyl)uracil (CT1817). Sodium hydride (365 mg, 16 mmol) was added to a stirring solution of 1-methyluracil (2.00 g, 16 mmol) in dimethyl sulfoxide (40 ml). After 15 min, 6-bromo-1-nonene (3.26 g, 16 mmol) was added and the mixture was stirred for 3 days. The reaction was then poured into 50 ml water and extracted with dichloromethane (3×60 ml). The organic layers were combined, washed with water (50 ml), and brine (30 ml) and dried (sodium sulfate). The solvent was evaporated to give CT1817 (3.72 g, 94% yield) as a colorless oil which solidified upon standing.

Example 33

This example illustrates the synthesis of 3-(10-Undecenyl)-1-methylhydrouracil (CT18 19). Sodium hydride (288 mg, 12 mmol) was added to a solution of N-methylhydrouracil (1.54 g, 12 mmol) and 1-bromo-10-undecene (2.33 g, 10 mmol) in 20 ml of dimethyl sulfoxide at room temperature and stirred for 12 hr. The reaction mixture was then quenched with water (80 ml) and extracted with dichloromethane (3×100 ml). The combined organic extract was washed with saturated brine solution (50 ml), dried over anhydrous magnesium sulfate and concentrated under reduced pressure. The crude product obtained was further purified by flash chromatography over silica gel (eluant: 20% acetone/hexane) to give the olefin CT1819 (2.04 g 61.8% yield).

Example 34

This example illustrates the synthesis of 3-(5-Hexenyl)-1-methylthymine (CT1905). Sodium hydride (343 mg, 14 mmol) was added to a stirring solution of 1-methylthymine (Sigma, 2.00 g, 14 mmol) in dimethylsulfoxide (30 ml). After 15 min, 6-bromo-1-hexene (Lancaster, 2.30 g, 14 mmol) was added and the mixture stirred for 69 hr. The reaction was then poured into 100 ml water and extracted with dichloromethane (4×50 ml). The organic layers were combined, washed with brine (40 ml) and dried (sodium sulfate). The solvent was evaporated to give a residue which was recrystallized in dichloromethane/ethyl ether to give CT1905 (2.80 g, 88% yield).

Example 35

This example illustrates the synthesis of 3-(6-cis-Nonenyl)-1-methylthymine. (CT1916). Sodium hydride (95%) (120 mg, 5 mmol) was added to a solution of 1-methylthymine (560 mg, 4 mmol) in dimethylsulfoxide (10 ml). After 20 min of stirring, 6-cis-nonenyl mesylate) (885 mg, 4 mmol) was added and stirred for 12 hr at room temperature. The reaction was warmed to 70°–80° C. and stirred for 4 hr. The reaction mixture was then poured into a separatory funnel containing 100 ml of water and extracted with dichloromethane (5×50 ml). The organic extracts were combined, washed with water (50 ml) and brine (50 ml), dried over anhydrous magnesium sulfate and concentrated under reduced pressure. The crude product obtained was further purified by flash chromatography over silica gel (eluant: 30% ethyl acetate/hexane) to give the olefin CT1916 (200 mg 19% yield).

Example 36

This example illustrates the synthesis of 1-Methyl-3-(8-nonenyl)thymine (CT1917). Sodium hydride (343 mg, 14 mmol) was added to a stirring solution of 1-methylthymine (2.00 g, 14 mmol) in dimethylsulfoxide (40 ml). After 15 min, 9-bromo-1-nonene (2.93 g, 14 mmol) was added and the mixture stirred for 20 hr. The reaction was poured into 40 ml water and extracted with dichloromethane (3×50 ml). The organic layers were combined, washed with water (40 ml), brine (20 ml), and dried (sodium sulfate). The solvent was evaporated to give CT1917 as a colorless oil which solidified upon standing (2.76 g, 73% yield).

Example 37

This example illustrates the synthesis of 1-(8-Nonenyl)-3,7-dimethylxanthine (CT1550). A mixture of theobromine (17.64 g, 98 mmol) and sodium hydride (2.35 g, 98 mmol) in dimethylsulfoxide (250 ml) was stirred for 15 min. After addition of 9-bromo-1-nonene (Alfebro, 20.0 g, 98 mmol) stirring was continued at ambient temperature for 3 days. The reaction mixture was then poured into water (300 ml) and extracted with dichloromethane (4×200 ml). The combined organic layers were washed with saturated aqueous salt solution (2×150 ml) and dried over sodium sulfate. The solvent was evaporated under vacuum to give a thick oil. After cooling a solution of the oil in a minimum of dichloromethane and ether, 1-(8 -nonenyl)-3,7-dimethylxanthine (CT1550) (24.34 g, 77.5 mmol, 99% yield) formed as white crystals.

Example 38

This example illustrates data regarding proliferative activity of various inventive compounds for inducting CMV promoter activity. The CMV promoter assay measures gene transcription and translation activity wherein any active compounds will have cytotoxic activity to inhibit cellular protein synthesis machinery in transformed (adenovirus) cells. Each compound was tested and the data is listed in Table 2 below. CT2544 was the most cytotoxic compound tested.

TABLE 2

| Compound | IC50 (µM) |
| --- | --- |
| CT1508 | 75 |
| CT1524 | 50 |
| CT1531 | 50 |
| CT1534 | >500 |
| CT1539 | >500 |
| CT1550 | 75 |
| CT1563 | 50 |
| CT1575 | >500 |
| CT1581 | >500 |
| CT1569R | >500 |
| CT1569S | 40 |
| CT2501 | 200 |
| CT2503 | >500 |
| CT2508 | >500 |
| CT2512 | 50 |
| CT2536R | 30 |
| CT2536S | 30 |
| CT2539 | >100 |
| CT2544 | 20 |
| CT2545 | 75 |
| CT1101 | 250 |
| CT1102 | 175 |
| CT1405 | 100 |
| CT1406 | 60 |
| CT1438 | >500 |

TABLE 2-continued

| Compound | IC50 (μM) |
|---|---|
| CT1441 | 300 |
| CT1604 | 100 |
| CT1814 | 100 |
| CT1817 | 250 |
| CT1812 | >100 |
| CT1905 | >500 |
| CT1916 | 250 |
| CT1917 | 75 |

Example 39

This example shows the effects of many inventive compounds on inhibition of mast cell degranulation by the serotonin release assay. This assay is described above and provides an in vitro model for an allergy and asthma therapeutic product. All of the compounds were tested at a concentration of 50 μM except for CT1604 which was tested at both 25 μM and 50 μM. We have highlighted in bold type the compounds with % inhibitions greater than 50%. Compounds with negative % inhibitions may be showing some toxicity at the concentration of 50 μM, such as CT1524. However CT1812 and CT1819 are probably not too toxic, they probably are just not having much of an effect at 50 μM. Compounds with % inhibitions greater than 100% may be inhibiting some of the spontaneous release normally seen in these cells, or may just indicate compounds that are totally inhibiting degranulation. Compounds with % inhibitions greater than 100% may be inhibiting some of the spontaneous release normally seen in these cells, or may just indicate compounds that are totally inhibiting degranulation.

Table 3 below shows the results of the studies with inventive compounds (see Table 1 for the chemical names).

TABLE 3

| COMPOUND | % INHIBITION (50 μM) | CHAIN LENGTH | CORE Group |
|---|---|---|---|
| 1539 | 35.76% | 6 | theobromine |
| 1101 | 74.49% | 6 | phthalimide |
| 1203 | 114.02% | 6 | benzoyleneurea |
| 1441 | 107.89% | 6 | methylpivaloylxanthine |
| 1812 | no inhibition | 6 | methyldihydrouracil |
| 1905 | 38.45% | 6 | methylthymine |
| 1550 | 13.42% | 9 | theobromine |
| 1102 | 71.06% | 9 | phthalimide |
| 1405 | 36.00% | 9 | 3-methylxanthine |
| 1411 | 87.89% | 9 | methylpivaloylxanthine |
| 1604 | 94.94% | 9 | glutarimide |
| 1817 | 55.51% | 9 | methyluracil |
| 1917 | 53.20% | 9 | methylthymine |
| 2501 | 68.82% | 11 | theobromine |
| 1406 | 59.42% | 11 | methylxanthine |
| 1403 | 84.23% | 11 | methylpivaloylxanthine |
| 1610 | 71.70% | 11 | glutarimide |
| 1823 | 41.14% | 11 | methyluracil |
| 1819 | no inhibition | 11 | methyldihydrouracil |
| 1931 | 72.24% | 11 | methylthymine |

TABLE 3-continued

| COMPOUND | % INHIBITION (50 μM) | CHAIN LENGTH | CORE Group |
|---|---|---|---|
| 1550 | 13.42% | 9 | theobromine |
| 2512 | 79.46% | 9 int. trans (20% cis) | theobromine |
| 1508 | 57.86% | 9 int. cis | theobromine |
| 1405 | 36.00% | 9 | 3-methylxanthine |
| 1442 | 63.38% | 9 int. cis | 3-methylxanthine |
| 1604 | 94.94% | 9 | glutarimide |
| 1607 | 52.34% | 9 int. cis | glutarimide |
| 1817 | 55.51% | 9 | methyluracil |
| 1814 | 25.90% | 9 int. cis | methyluracil |
| 1917 | 53.20% | 9 | methylthymine |
| 1916 | 24.92% | 9 int. cis | methylthymine |
| 1101 | 74.49% | 6 | phthalimide |
| 1102 | 71.06% | 9 | phthalimide |
| 1203 | 114.02% | 6 | benzoyleneurea |
| 1405 | 36.00% | 9 | 3-methylxanthine |
| 1406 | 59.42% | 11 | methylxanthine |
| 1441 | 107.89% | 6 | methylpivaloylxanthine |
| 1411 | 87.89% | 9 | methylpivaloylxanthine |
| 1403 | 84.23% | 11 | methylpivaloylxanthine |
| 1604 | 94.94% | 9 | glutarimide |
| 1610 | 71.70% | 11 | glutarimide |
| 1817 | 55.51% | 9 | methyluracil |
| 1823 | 41.14% | 11 | methyluracil |
| 1812 | no inhibition | 6 | methyldihydrouracil |
| 1819 | no inhibition | 11 | methyldihydrouracil |
| 1905M | 38.45% | 6 | methylthymine |
| 1917 | 53.20% | 9 | methylthymine |
| 1931 | 72.24% | 11 | methylthymine |

There appears to be a bimodal distribution of compounds such that the C5 compound (CT1575) and the C11 compound (CT2501) are the two most potent compounds in this group. However, two C6 compounds CT1203 (3-methylbenzoyleneurea core), CT1441 (3-methyl-7-methylpivaloylxanthine core), and one C9 compound, CT1604 (glutarimide core), appear to be quite potent. The C6 compounds appear to be the most potent, irrespective of the core moiety.

Moreover, changing a terminal olefin to an internal double bond on a theobromine core appears to increase the activity of these compounds, especially for the C9 chain length (CT1550 vs. CT2512) and the C10 chain length (CT1563 vs. CT2560) compounds. At least for the C9 chain length compounds, a trans double bonds appear to be more active than the cis.

Changing a terminal olefin to an internal double bond on both theobromine cores (CT1550 vs. CT2512 and CT1508) and 3-methylxanthine cores (CT1405 vs. CT1442) increases the activity of these compounds. However, changing a terminal olefin to an internal double bond on a glutarimide core (CT1604 vs. CT1607), methyluracil core (CT1817 vs. CT1814), and methylthymine core (CT1917 vs. CT1916) appears to decrease the activity of these compounds. These structure-activity comparisons are shown in Tables 4 and 5 below.

TABLE 4

| TREATMENT | RELEASE | RELEASE X2 | INCORP | TOTAL | % RELEASE | AVERAGE | STD DEV 5 | RELEASE-SPONT | % INHIBITION |
|---|---|---|---|---|---|---|---|---|---|
| spont. | 2553 | 5106 | 25170 | 30276 | 16.86% | 16.56% | 0.44% | | |

TABLE 4-continued

| TREATMENT | RELEASE | RELEASE X2 | INCORP | TOTAL | % RELEASE | AVERAGE | STD DEV 5 | RELEASE-SPONT | % INHIBITION |
|---|---|---|---|---|---|---|---|---|---|
| | 2527 | 5054 | 26055 | 31109 | 16.25% | | | | |
| EtOH | 3428 | 6856 | 23185 | 30041 | 22.82% | 22.33% | 0.69% | 5.78% | |
| | 3327 | 6654 | 23806 | 30460 | 21.85% | | | | |
| DNP | 3620 | 7240 | 22109 | 29349 | 24.67% | 24.58% | 0.13% | 8.02% | |
| | 3608 | 7216 | 22257 | 29473 | 24.48% | | | | |
| 1508 | 3101 | 6202 | 23345 | 29547 | 20.99% | 19.94% | 1.49% | 3.38% | 57.86% |
| | 2833 | 5666 | 24345 | 30011 | 18.88% | | | | |
| 1524 | 4581 | 9162 | 21234 | 30396 | 30.14% | 30.46% | 0.45% | 13.90% | −73.32% |
| | 4693 | 9386 | 21116 | 30502 | 30.77% | | | | |
| 1531 | 3260 | 6520 | 22045 | 28565 | 22.83% | 23.55% | 1.02% | 6.99% | 12.85% |
| | 3316 | 6632 | 20698 | 27330 | 24.27% | | | | |
| 1534 | 3466 | 6932 | 25050 | 31982 | 21.67% | 22.02% | 0.49% | 5.47% | 31.85% |
| | 3455 | 6910 | 23982 | 30892 | 22.37% | | | | |
| 1539 | 3210 | 6420 | 23296 | 29716 | 21.60% | 21.71% | 0.15% | 5.15% | 35.76% |
| | 3379 | 6758 | 24225 | 30983 | 21.81% | | | | |
| 1550 | 3691 | 7382 | 25575 | 32957 | 22.40% | 23.50% | 1.56% | 6.94% | 13.42% |
| | 3920 | 7840 | 24029 | 31869 | 24.60% | | | | |
| 1563 | 3537 | 7074 | 22768 | 29842 | 23.70% | 23.98% | 0.39% | 7.43% | 7.39% |
| | 3629 | 7258 | 22657 | 29915 | 24.26% | | | | |
| 1575 | 2984 | 5968 | 22907 | 28875 | 20.67% | 20.89% | 0.31% | 4.33% | 45.98% |
| | 3219 | 6438 | 24063 | 30501 | 21.11% | | | | |
| 1581 | 3168 | 6336 | 24336 | 30672 | 20.66% | 20.87% | 0.29% | 4.31% | 46.26% |
| | 3101 | 6202 | 23227 | 29429 | 21.07% | | | | |
| 1596R | 3594 | 7188 | 23361 | 30549 | 23.53% | 23.14% | 0.54% | 6.59% | 17.85% |
| | 3548 | 7096 | 24082 | 31178 | 22.76% | | | | |
| 1596S | 3021 | 6042 | 24740 | 30782 | 19.63% | 19.71% | 0.11% | 3.15% | 60.73% |
| | 2968 | 5936 | 24071 | 30007 | 19.78% | | | | |
| 2501 | 2940 | 5880 | 25161 | 31041 | 18.94% | 19.06% | 0.16% | 2.50% | 68.82% |
| | 2817 | 5634 | 23755 | 29389 | 19.17% | | | | |
| 2503 | 3318 | 6636 | 23885 | 30521 | 21.74% | 21.43% | 0.45% | 4.87% | 39.25% |
| | 3236 | 6472 | 24182 | 30654 | 21.11% | | | | |
| 2508M | 2657 | 5314 | 23055 | 28369 | 18.73% | 19.44% | 1.01% | 2.89% | 64.00% |
| | 2804 | 5608 | 22217 | 27825 | 20.15% | | | | |
| 2512 | 2758 | 5516 | 24476 | 29992 | 18.39% | 18.20% | 0.27% | 1.65% | 79.46% |
| | 2604 | 5208 | 23702 | 28910 | 18.01% | | | | |
| 2516 | 3230 | 6460 | 24860 | 31320 | 20.63% | 22.12% | 2.12% | 5.57% | 30.60% |
| | 3693 | 7386 | 23887 | 31273 | 23.62% | | | | |
| 2536R | 2335 | 4670 | 24293 | 28963 | 16.12% | 16.00% | 0.17% | −0.55% | 106.92% |
| | 2357 | 4714 | 24976 | 29690 | 15.88% | | | | |
| 2536S | 2425 | 4850 | 24695 | 29545 | 16.42% | 16.76% | 0.49% | 0.21% | 97.39% |
| | 2487 | 4974 | 24091 | 29065 | 17.11% | | | | |
| 2539 | 2823 | 5646 | 23976 | 29622 | 19.06% | 19.69% | 0.88% | 3.13% | 60.97% |
| | 2789 | 5578 | 21885 | 27463 | 20.31% | | | | |
| 2544 | 2294 | 4588 | 25365 | 29953 | 15.32% | 15.44% | 0.18% | −1.11% | 113.86% |
| | 2260 | 4520 | 24509 | 29029 | 15.57% | | | | |
| 2545 | 2718 | 5436 | 23707 | 29143 | 18.65% | 19.05% | 0.56% | 2.49% | 68.91% |
| | 2657 | 5314 | 22015 | 27329 | 19.44% | | | | |
| 2555 | 3450 | 6900 | 22367 | 29267 | 23.58% | 21.68% | 2.68% | 5.72% | 36.12% |
| | 2994 | 5988 | 24281 | 30269 | 19.78% | | | | |
| 2560 | 2990 | 5980 | 23958 | 29938 | 19.97% | 19.51% | 0.65% | 2.96% | 63.12% |
| | 2549 | 5098 | 21660 | 26758 | 19.05% | | | | |
| 1101 | 2487 | 4974 | 21980 | 26954 | 18.45% | 18.60% | 0.21% | 2.05% | 74.49% |
| | 2626 | 5252 | 22760 | 28012 | 18.75% | | | | |
| 1102 | 2471 | 4942 | 20469 | 25411 | 19.45% | 18.88% | 0.81% | 2.32% | 71.06% |
| | 2770 | 5540 | 24724 | 30264 | 18.31% | | | | |
| 1203 | 2075 | 4150 | 20532 | 24682 | 16.81% | 15.43% | 1.96% | −1.12% | 114.02% |
| | 2013 | 4026 | 24633 | 28659 | 14.05% | | | | |
| 1405 | 2838 | 5676 | 20030 | 25706 | 22.08% | 21.69% | 0.55% | 5.13% | 36.00% |
| | 3047 | 6094 | 22521 | 28615 | 21.30% | | | | |
| 1406 | 2881 | 5762 | 24520 | 30282 | 19.03% | 19.81% | 1.11% | 3.26% | 59.42% |
| | 3267 | 6534 | 25195 | 31729 | 20.59% | | | | |
| 1442 | 2810 | 5620 | 23434 | 29054 | 19.34% | 19.49% | 0.21% | 2.94% | 63.38% |
| | 2965 | 5930 | 24260 | 30190 | 19.64% | | | | |
| 1403 | 2443 | 4886 | 23246 | 28132 | 17.37% | 17.82% | 0.64% | 1.26% | 84.23% |
| | 2872 | 5744 | 25691 | 31435 | 18.27% | | | | |
| 1411 | 2484 | 4968 | 24627 | 29595 | 16.79% | 17.53% | 1.05% | 0.97% | 87.89% |
| | 2756 | 5512 | 24663 | 30175 | 18.27% | | | | |
| 1441 | 2125 | 4250 | 22567 | 26817 | 15.85% | 15.92% | 0.11% | −0.63% | 107.89% |
| | 2308 | 4616 | 24238 | 28854 | 16.00% | | | | |
| 1604 (50 uM) | 2419 | 4838 | 24224 | 29062 | 16.65% | 16.96% | 0.44% | 0.41% | 94.94% |
| | 2602 | 5204 | 24920 | 30124 | 17.28% | | | | |
| 1604 (25 uM) | 3332 | 6664 | 25328 | 31992 | 20.83% | 21.41% | 0.82% | 4.85% | 39.49% |
| | 3466 | 6932 | 24595 | 31527 | 21.99% | | | | |
| 1607 | 3439 | 6878 | 25461 | 32339 | 21.27% | 20.38% | 1.26% | 3.82% | 52.34% |
| | 3027 | 6054 | 25012 | 31066 | 19.49% | | | | |
| 1610 | 2991 | 5982 | 24247 | 30229 | 19.79% | 18.83% | 1.36% | 2.27% | 71.70% |

TABLE 4-continued

| TREATMENT | RELEASE | RELEASE X2 | INCORP | TOTAL | % RELEASE | AVERAGE | STD DEV 5 | RELEASE-SPONT | % INHIBITION |
|---|---|---|---|---|---|---|---|---|---|
| | 2694 | 5388 | 24776 | 30164 | 17.86% | | | | |
| 1814 | 3157 | 6314 | 23589 | 29903 | 21.11% | 22.50% | 1.96% | 5.94% | 25.90% |
| | 3500 | 7000 | 22311 | 29311 | 23.88% | | | | |
| 1817 | 3095 | 6190 | 23565 | 29755 | 20.80% | 20.12% | 0.96% | 3.57% | 55.51% |
| | 2853 | 5706 | 23640 | 29346 | 19.44% | | | | |
| 1812 | 3629 | 7258 | 21391 | 28649 | 25.33% | 24.83% | 0.72% | 8.27% | -3.14% |
| | 3885 | 7770 | 24177 | 31947 | 24.32% | | | | |
| 1819 | 4099 | 8198 | 22191 | 30389 | 26.98% | 25.98% | 1.41% | 9.42% | -17.47% |
| | 3778 | 7556 | 22696 | 30252 | 24.98% | | | | |
| 1823 | 3251 | 6502 | 24419 | 30921 | 21.03% | 21.28% | 0.35% | 4.72% | 41.14% |
| | 3312 | 6624 | 24150 | 30774 | 21.52% | | | | |
| 1905 | 3289 | 6578 | 23996 | 30574 | 21.52% | 21.49% | 0.03% | 4.94% | 38.45% |
| | 3315 | 6630 | 24252 | 30882 | 21.47% | | | | |
| 1916 | 3331 | 6662 | 23089 | 29751 | 22.39% | 22.58% | 0.26% | 6.02% | 24.92% |
| | 3364 | 6728 | 22830 | 29558 | 22.76% | | | | |
| 1917 | 3110 | 6220 | 24059 | 30279 | 20.54% | 20.31% | 0.33% | 3.75% | 53.20% |
| | 2955 | 5910 | 23529 | 29439 | 20.08% | | | | |
| 1931 | 2932 | 5864 | 25345 | 31209 | 18.79% | 18.78% | 0.01% | 2.23% | 72.24% |
| | 2736 | 5472 | 23675 | 29147 | 18.77% | | | | |

TABLE 5

| COMPOUND (50 μM) | % INHIBITION |
|---|---|
| 1508 | 57.86% |
| 1524 | -73.32% |
| 1531 | 12.85% |
| 1534 | 31.85% |
| 1539 | 35.76% |
| 1550 | 13.42% |
| 1563 | 7.39% |
| 1575 | 45.98% |
| 1581 | 46.26% |
| 1596R | 17.85% |
| 1596S | 60.73% |
| 2501 | 68.82% |
| 2503 | 39.25% |
| 2508 | 64.00% |
| 2512 | 79.46% |
| 2516 | 30.60% |
| 2536R | 106.92% |
| 2536S | 97.39% |
| 2539 | 60.97% |
| 2544 | 113.86% |
| 2545 | 68.91% |
| 2555 | 36.12% |
| 2560 | 63.12% |
| 1101 | 74.49% |
| 1102 | 71.06% |
| 1203 | 114.02% |
| 1405 | 36.00% |
| 1406 | 59.42% |
| 1442 | 63.38% |
| 1403 | 84.23% |
| 1411 | 87.89% |
| 1441 | 107.89% |
| 1604 (50 μM) | 94.94% |
| 1604 (25 μM) | 39.49% |
| 1607 | 52.34% |
| 1610 | 71.70% |
| 1814 | 25.90% |
| 1817 | 55.51% |
| 1812 | -3.14% |
| 1819 | -17.47% |
| 1823 | 41.14% |
| 1905 | 38.45% |
| 1916 | 24.92% |
| 1917 | 53.20% |
| 1931 | 72.24% |

Example 40

Figure 1:
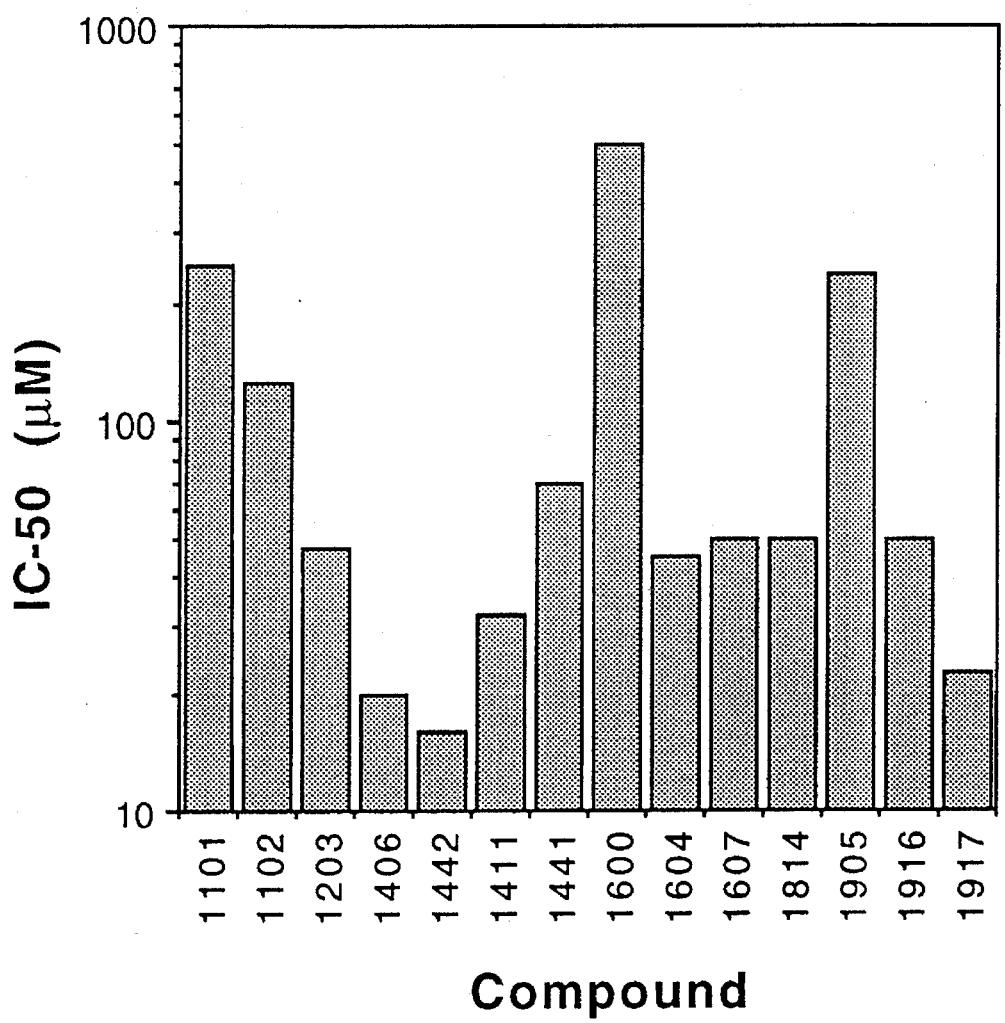
FIG. 1 shows a mixed lymphocyte reaction assay of fourteen inventive compounds by showing the IC50 value of each compound in this assay. The mixed lymphocyte reaction shows a proliferative response of PBMC (peripheral blood mononuclear cells) to allogeneic stimulation determined in a two-way mixed lymphocyte reaction. CT1442 and CT1406, both having a 3-methyl xanthine core moiety showed the most potent activity.
Figure 2:
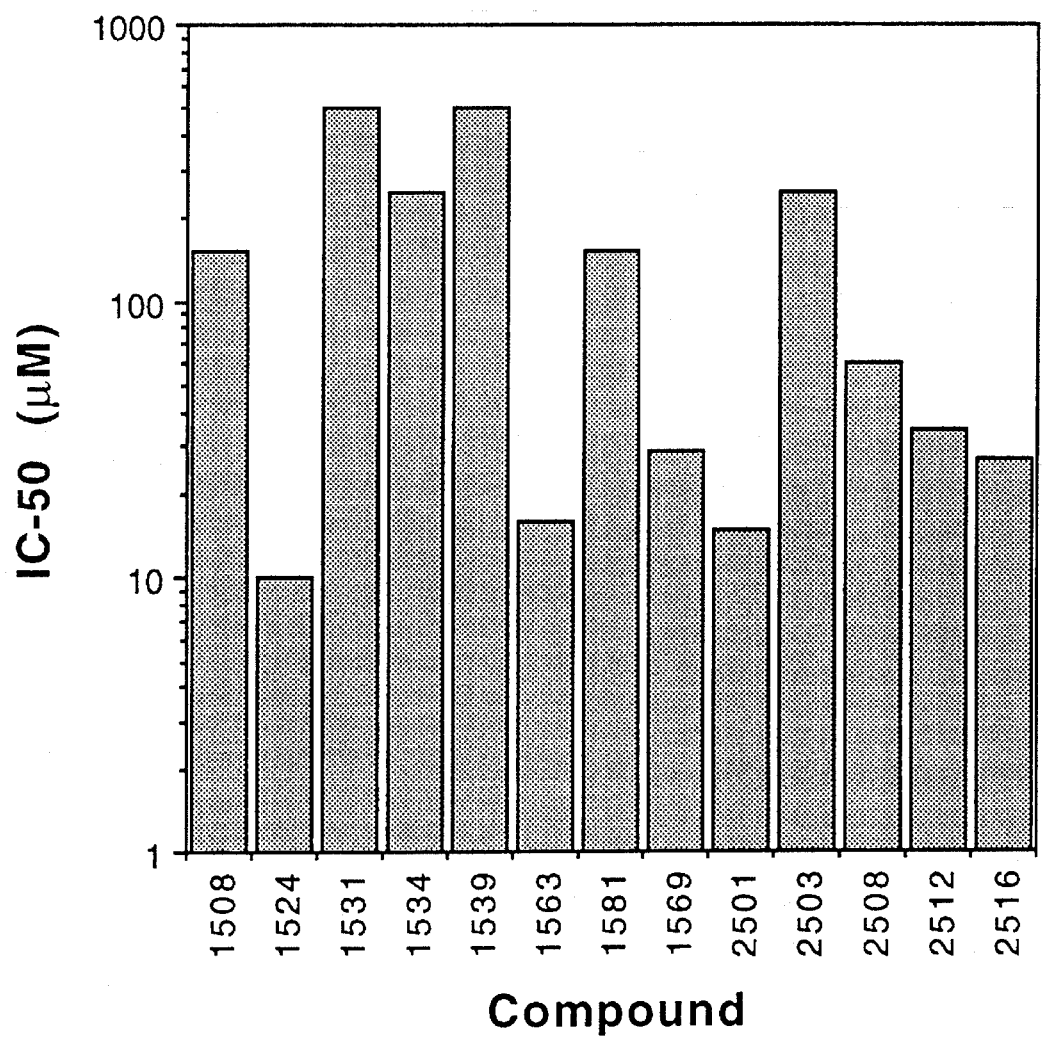
FIG. 2 shows a mixed lymphocyte reaction assay of thirteen inventive compounds by showing the IC50 value of each compound in this assay. The mixed lymphocyte reaction shows a proliferative response of PBMC (peripheral blood mononuclear cells) to allogeneic stimulation determined in a two-way mixed lymphocyte reaction. Only CT1524, CT1563 and CT2501 showed activity within dose ranges achievable in vivo.
Figure 3:
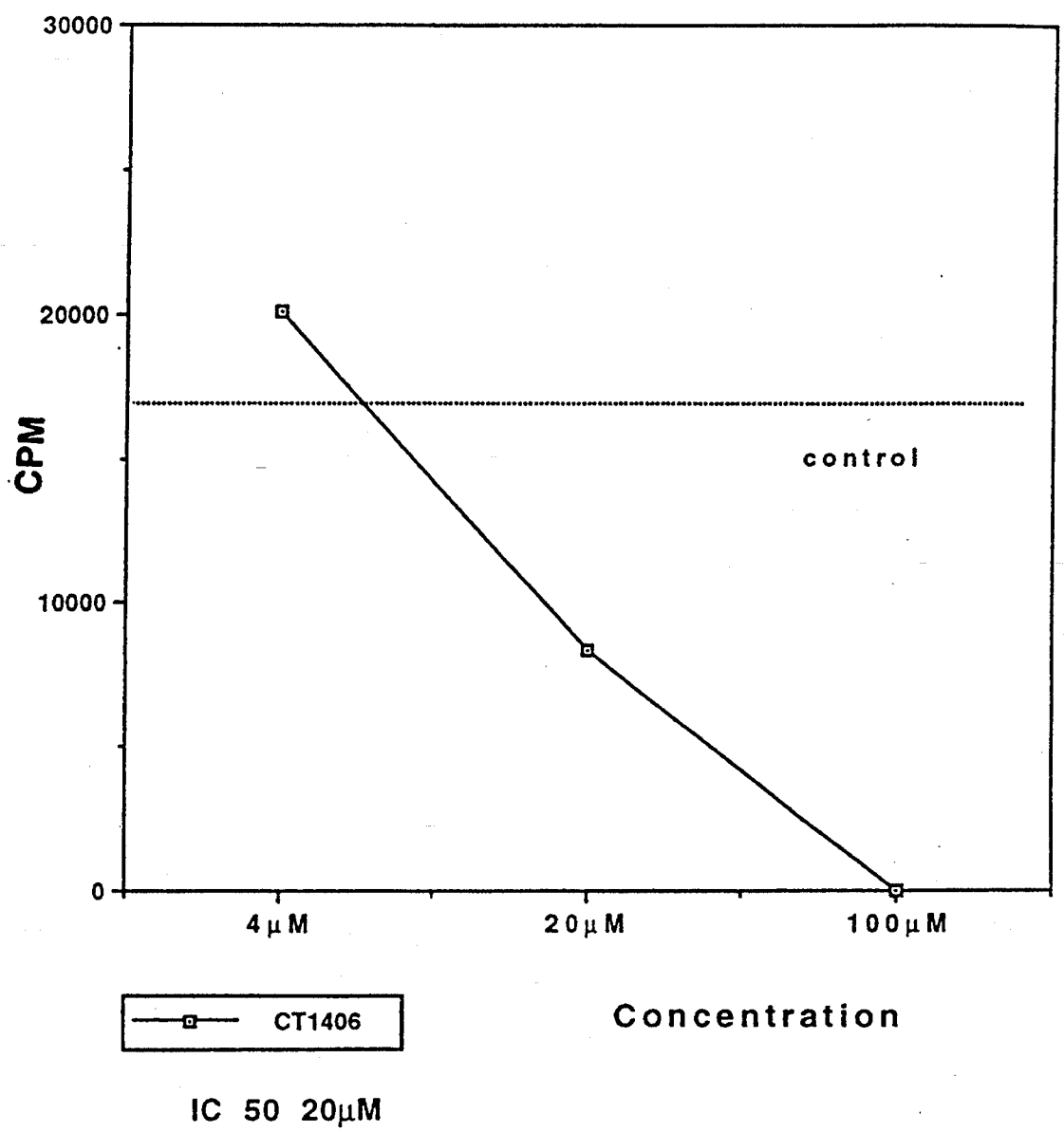
FIGS. 3 and 4 show a mixed lymphocyte reaction assay of CT1406 (1-(10-undecenyl)-3-methylxanthine) and CT1403 1-(10-undecenyl)-3-methyl-7-methylpivaloylxanthine. The mixed lymphocyte reaction shows a proliferative response of PBMC to allogeneic stimulation determined in a two-way mixed lymphocyte reaction. CT1406 and CT1403 showed dose response activity in this immune modulating activity assay procedure with an IC50 of 20 μM for CT1406 and 10 μM for CT1403.
Figure 4:
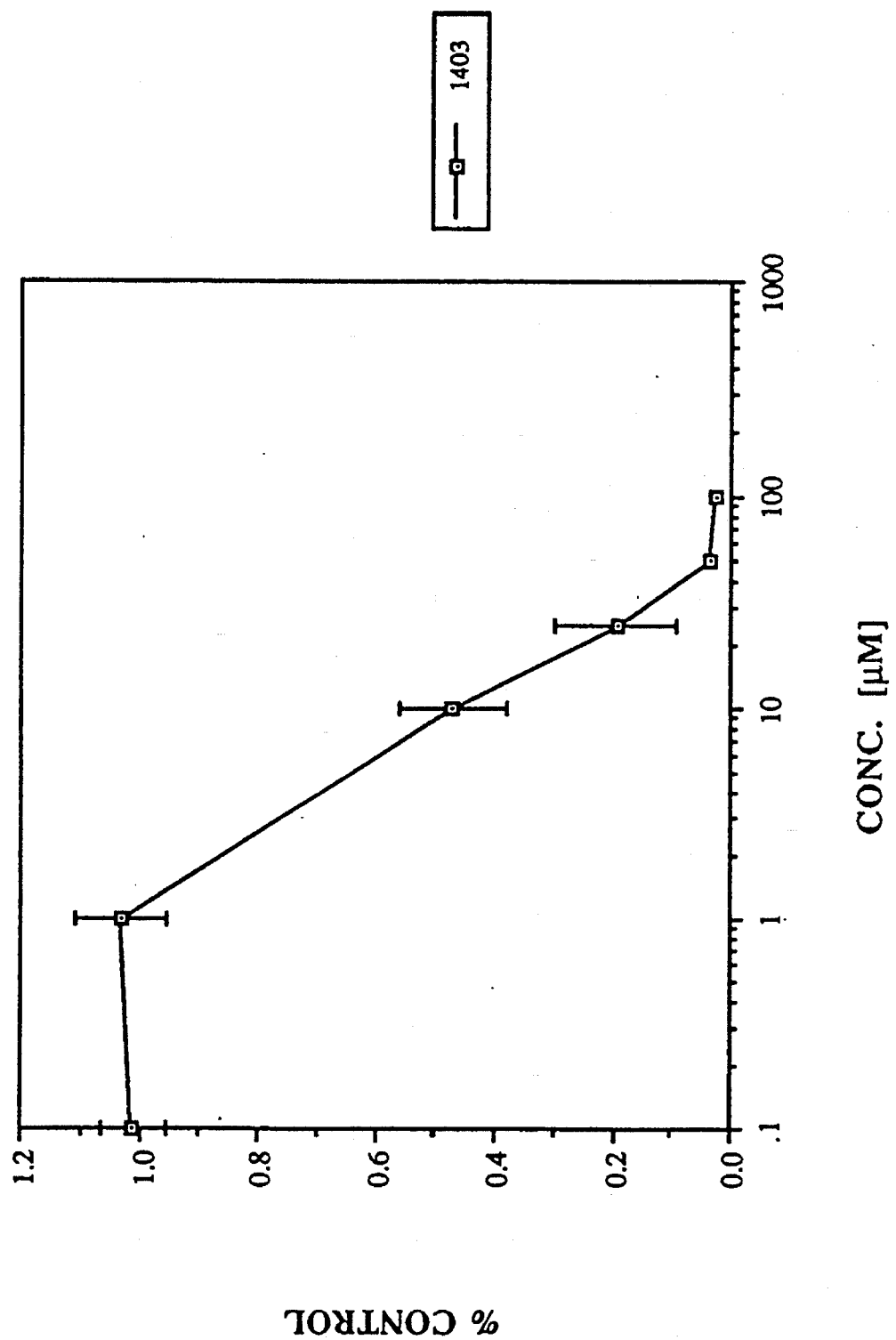

This example illustrates a mixed lymphocyte reaction assay of inventive compounds by showing the IC50 value of each compound in this assay and a dose response of several compounds to illustrate an IC50 determination. The mixed lymphocyte reaction shows a proliferative response of PBMC (peripheral blood mononuclear cells) to allogeneic stimulation determined in a two-way mixed lymphocyte reaction. In FIG. 1, CT1442 and CT1406, both having a 3-methyl xanthine core moiety showed the most potent activity. In FIG. 2, only CT1524, CT1563 and CT2501 showed activity within dose ranges achievable in vivo. In FIGS. 3 and 4 CT1406 and CT1403 showed dose response activity in this immune modulating activity assay procedure with an IC50 of 20 μM for CT1406 and 10 μM for CT1403.

Figure 5:
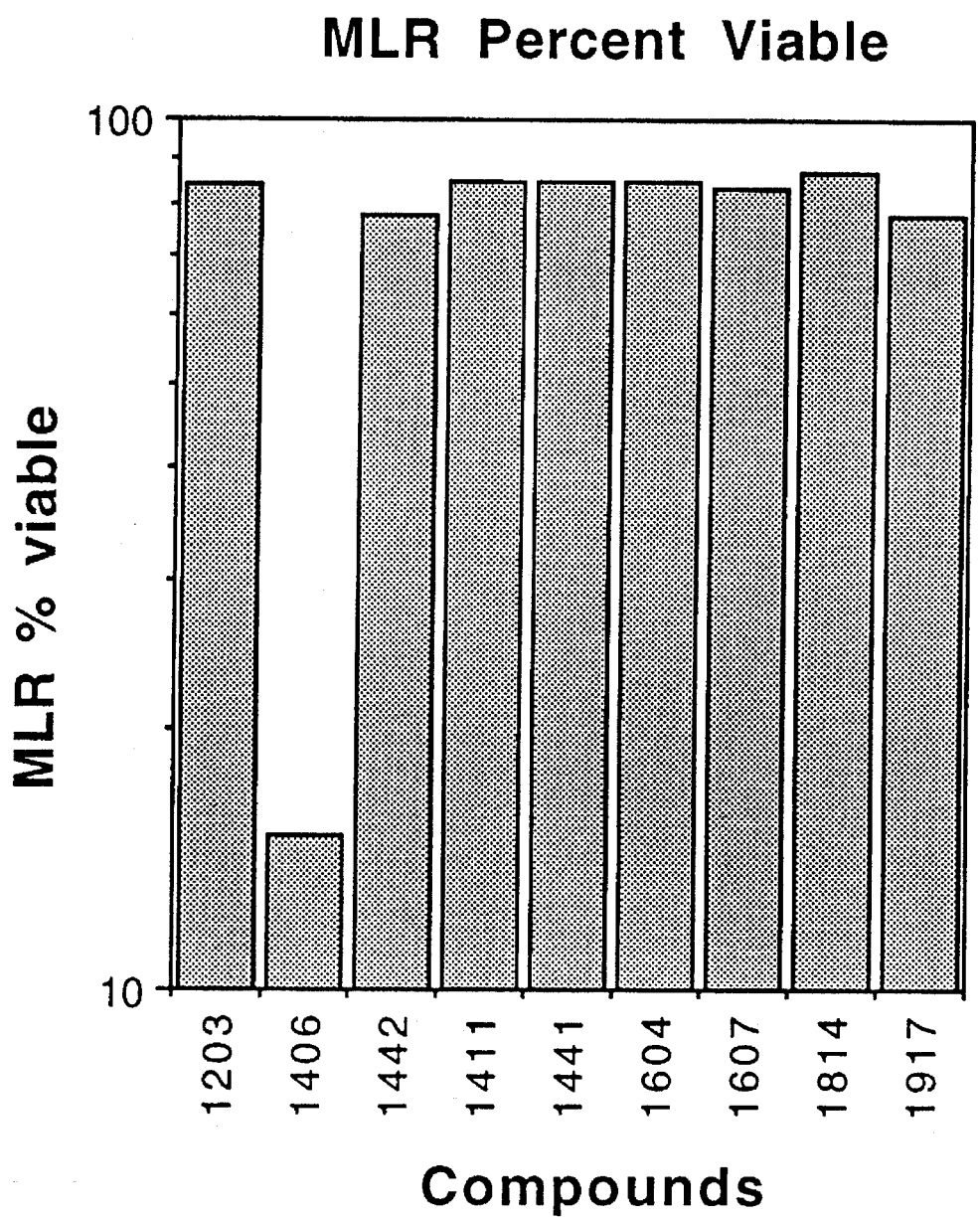
FIG. 5 shows a bar graph of the percent viable cells in mixed lymphocyte assay culture after six days of cell culture with nine inventive compounds. Control cells that have not been exposed to a drug are generally 78 to 85% viable under such culture conditions. For this graph, all of the compounds were present at 100 μM, which is usually well above their IC50 concentration in this assay (see FIGS. 1 and 2). One of the most potent compounds, CT1406, also was the most cytotoxic at 100 μM, but this concentration is well above its IC50 value indicating the presence of a significant therapeutic window. Also effective compound CT1442 showed little or no cytotoxicity at concentrations well above its effective concentrations.
Figure 6:
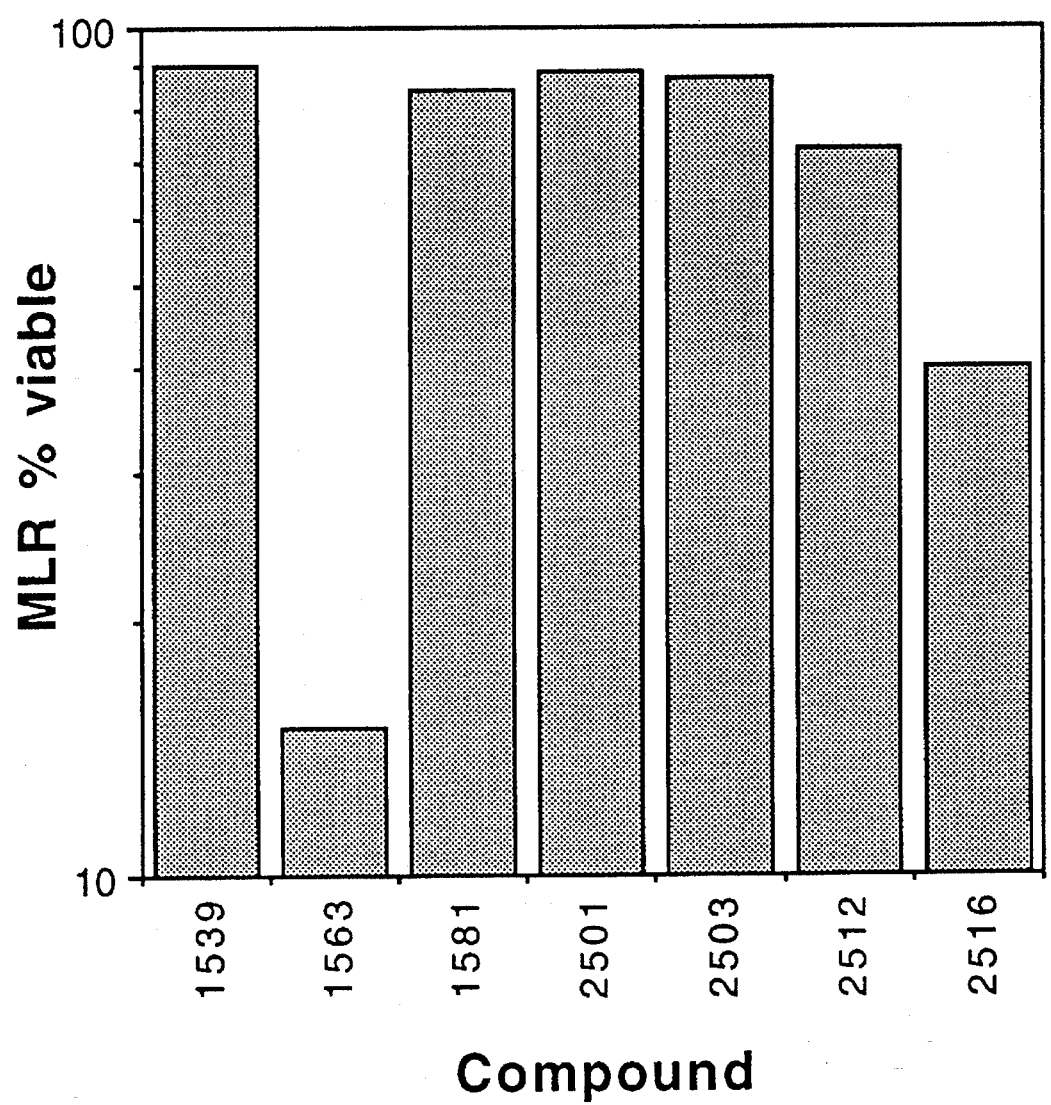
FIG. 6 shows a bar graph of the percent viable cells in mixed lymphocyte assay culture after six days of cell culture with seven inventive compounds. Control cells that have not been exposed to a drag are generally 78% to 85% viable under such culture conditions. For this graph, all of the compounds were present at 100 μM, which is usually well above their IC50 concentration in this assay (see FIGS. 1 and 2). One of the most potent compounds, CT1563, also was the most cytotoxic at 100 μM, but this concentration is well above its IC50 value indicating the presence of a significant therapeutic window. Also effective compound CT2501 showed little or no cytotoxicity at concentrations well above its effective concentrations.

FIGS. 5 and 6 show a bar graph of the percent viable cells in mixed lymphocyte assay culture after six days of cell culture with nine inventive compounds. Control cells that have not been exposed to a drug are generally 78 to 85% viable under such culture conditions. For this graph, all of the compounds were present at 100 μM, which is usually well above their IC50 concentration in this assay (see FIGS. 1 and 2). One of the most potent compounds, CT1406, also was the most cytotoxic at 100 μM, but this concentration is well above its IC50 value indicating the presence of a significant therapeutic window. Also effective compound CT1442 showed little or no cytotoxicity at concentrations well above its effective concentrations. One of the most potent compounds, CT1563, also was the most cytotoxic at 100 μM, but this concentration is well above its IC50 value indicating the presence of a significant therapeutic window. Also effective compound CT2501 showed little or no cytotoxicity at concentrations well above its effective concentrations.

Example 41

Figure 7:
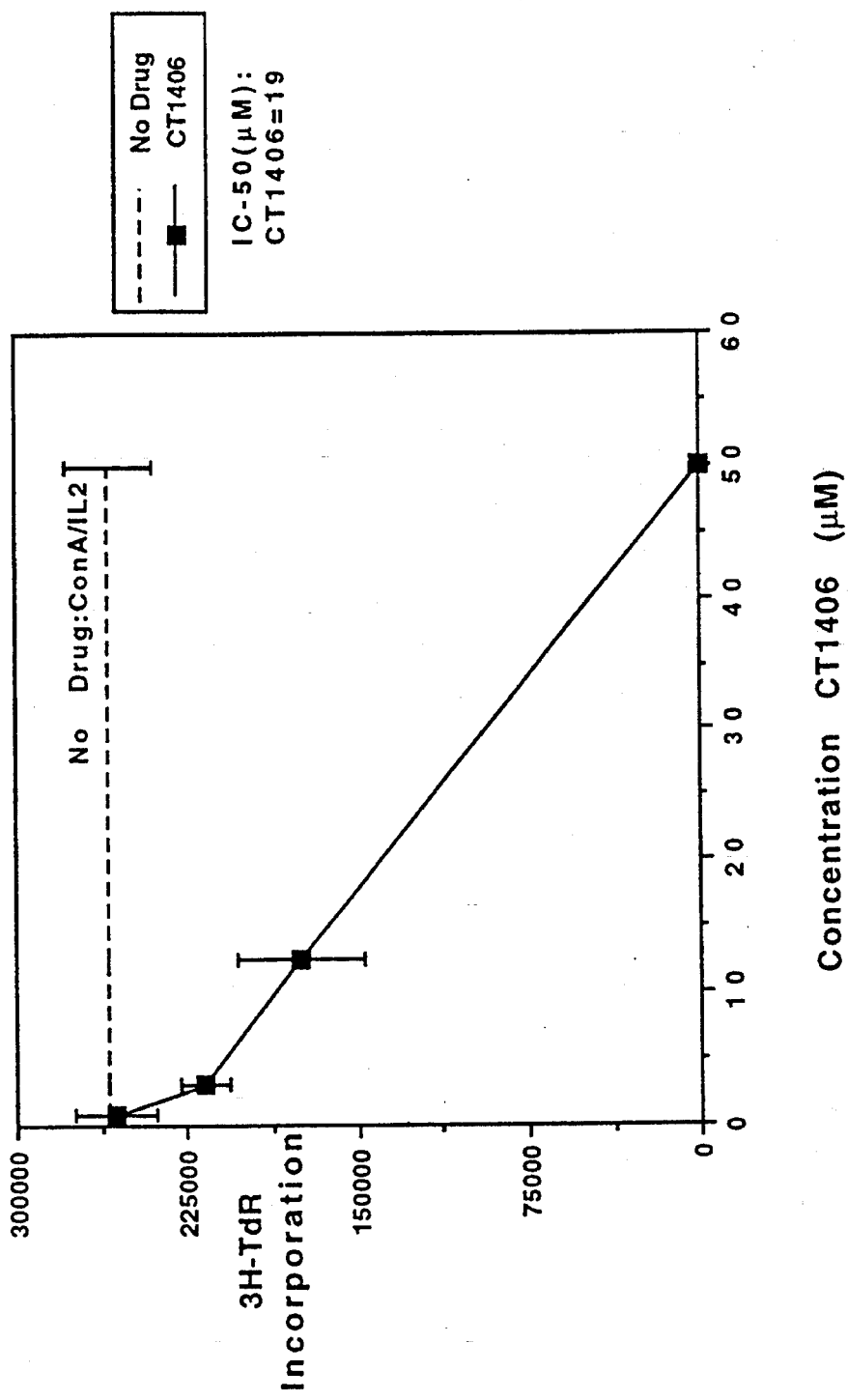
FIG. 7 shows the effects of CT1406 on inhibition of murine thymocyte proliferation stimulated by Concanavalin A (ConA) and interleukin-1 alpha (IL-1α). CT1408 was added to the cells at the doses indicated two hours prior to activation with ConA and IL-1α. CT1408 inhibited thymocyte proliferation in a dose-response manner with an IC50 of about 19 μM, as is shown in FIG. 7. Background counts were less than 200 cpm.

This example illustrates the effects of several inventive compounds, including CT1406, on inhibition of murine thymocyte proliferation stimulated by Concanavalin A (ConA) and interleukin-1 alpha (IL-1α) or interleukin-2 (IL-2). CT1408 was added to the cells at the doses indicated two hours prior to activation with ConA and IL-1α. CT1408 inhibited thymocyte proliferation in a dose-response manner with an IC50 of about 19 μM, as is shown in FIG. 7. Background counts were less than 200 cpm. These data indicate immune suppression activity for CT1406 and applications for treatment of autoimmune disorders and acute and chronic inflammatory diseases.

Figure 8:
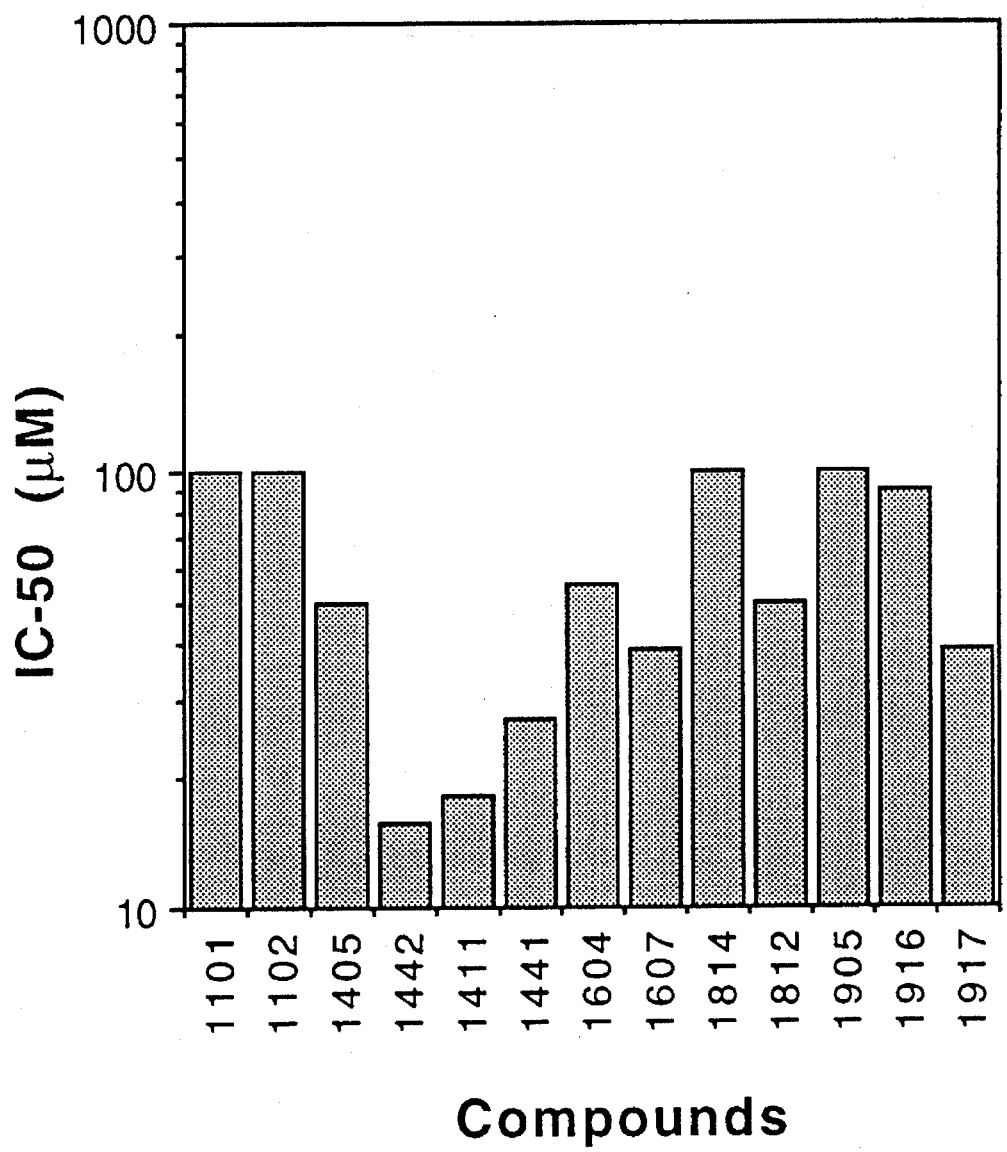
FIG. 8 compares T cell immune suppression data of thirteen inventive compounds by comparing their IC50 values in a murine thymocyte stimulated by ConA and IL-2 in vitro model. CT1442, CT1411 and CT1441 showed potent immune suppressing activity.

FIG. 8 compares T cell immune suppression data of thirteen inventive compounds by comparing their IC50 values in a murine thymocyte stimulated by ConA and IL-2 in vitro model. CT1442, CT1411 and CT1441 showed potent immune suppressing activity.

Figure 9:
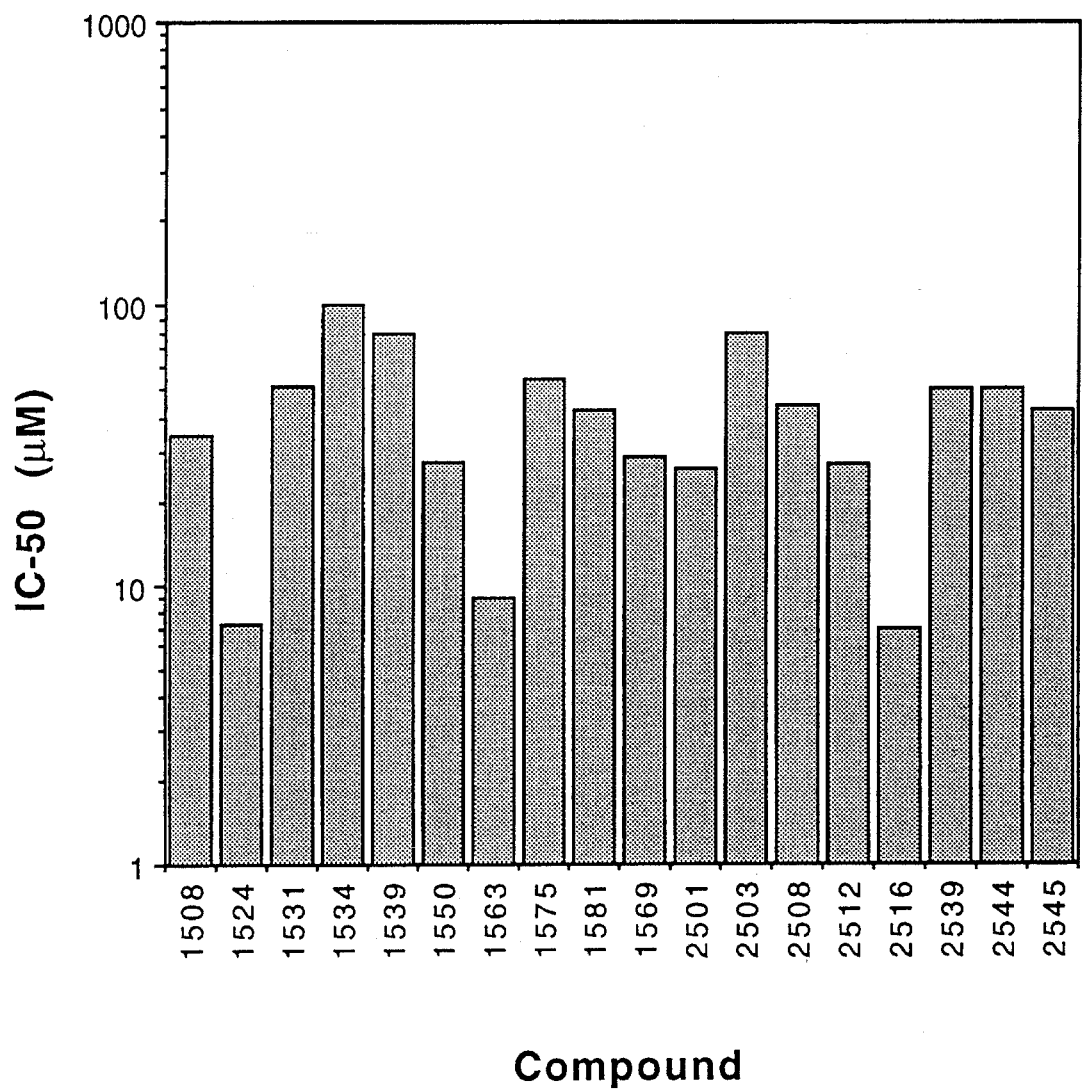
FIG. 9 compares T cell immune suppression data of eighteen inventive compounds by comparing their IC50 values in a murine thymocyte stimulated by ConA and IL-2 in vitro model. CT1524, CT1563 and CT2616 showed potent immune suppressing activity.

FIG. 9 compares T cell immune suppression data of eighteen inventive compounds by comparing their IC50 values in a murine thymocyte stimulated by ConA and IL-2 in vitro model. CT1524, CT1563 and CT2616 showed potent immune suppressing activity.

Example 42

Figure 10:
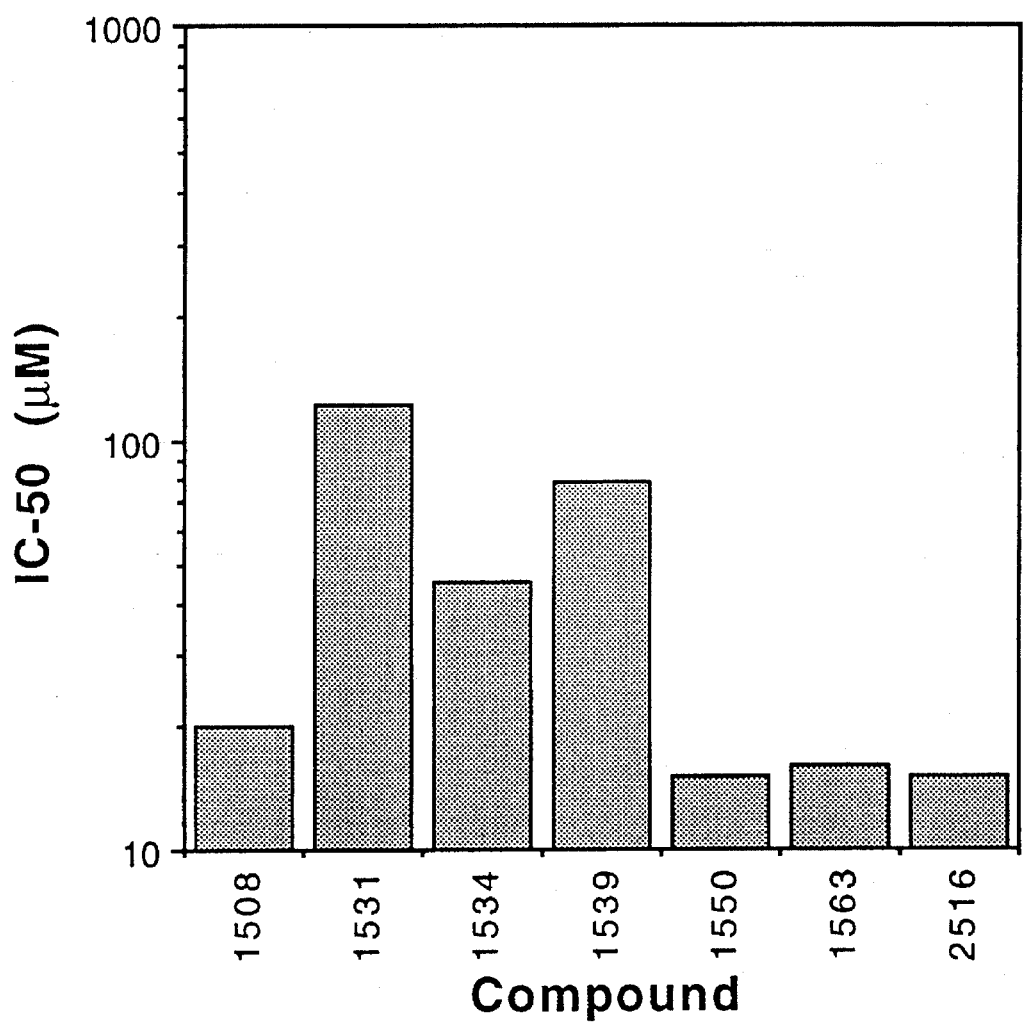
FIG. 10 shows the effects of seven inventive compounds on inhibition of murine splenocyte proliferation stimulated by anti-mu (10 μg/ml) and interleukin-4 (IL-4, 12.5 ng/ml). Drug was added to the cells at the doses indicated two hours prior to activation with anti-mu and IL-4. CT1508, CT1550, CT1563 and CT2516 inhibited splenocyte proliferation in a dose-response manner with an IC50 below 10 μM for each drug, as is shown in FIG. 10. Background counts were less than 200 cpm. This assay is an in vitro model for various autoimmune diseases.

This example illustrates the effects of seven inventive compounds on inhibition of murine splenocyte proliferation stimulated by anti-mu (10 μg/ml) and interleukin-4 (IL-4, 12.5 ng/ml). Drug was added to the cells at the doses indicated two hours prior to activation with anti-mu and IL-4. CT1508, CT1550, CT1563 and CT2516 inhibited splenocyte proliferation in a dose-response manner with an IC50 below 10 μM for each drug, as is shown in FIG. 10. Background counts were less than 200 cpm. This assay is an in vitro model for various autoimmune diseases.

Example 43

Figure 11:
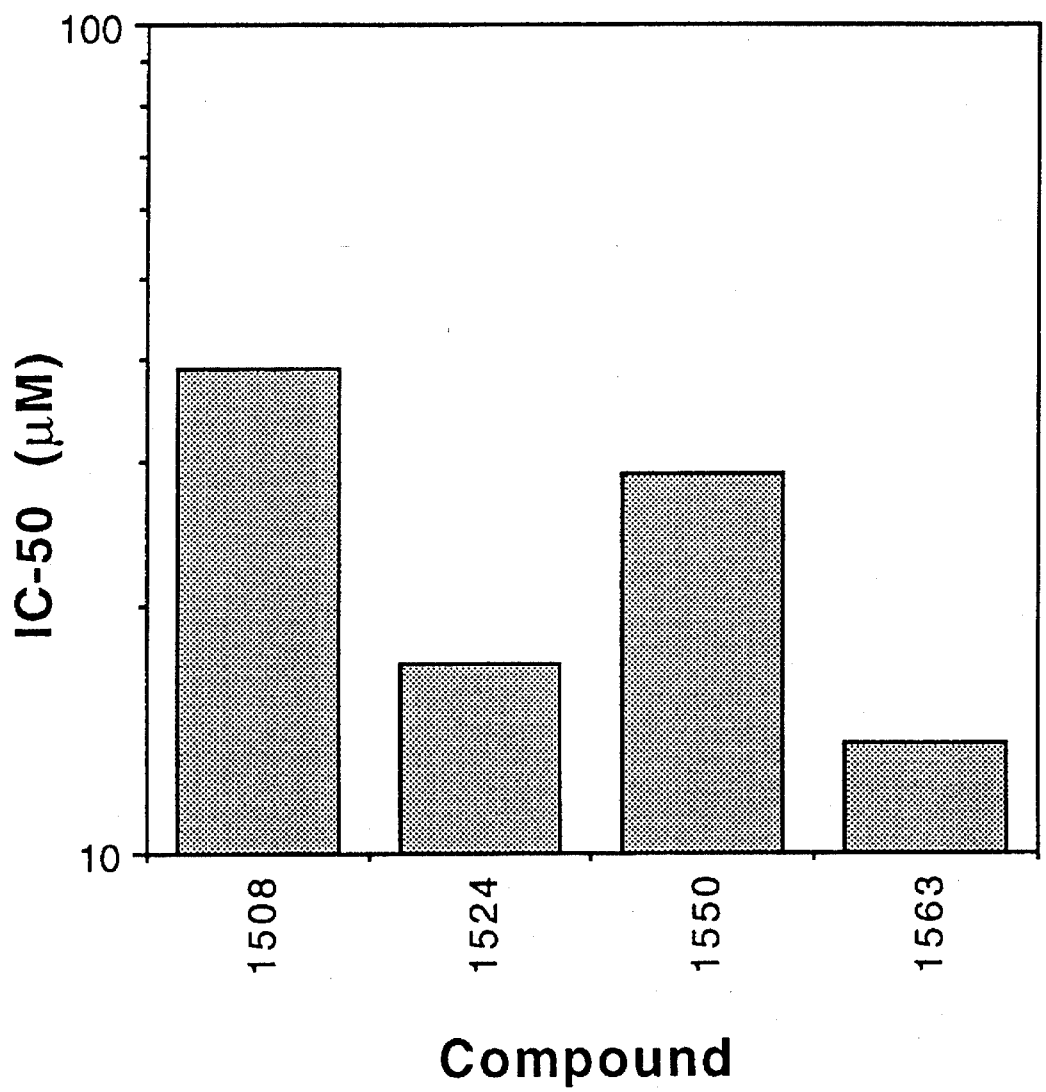
FIG. 11 shows the effects of four inventive compounds on inhibition of murine lymph node cell proliferation stimulated by antigen. This assays uses murine T cells that proliferate in vitro in response to a soluble protein antigen that is first used to prime the T cells in vivo. Drug was added to the cells at the doses indicated two hours prior to activation with alloantigen. Each drug inhibited T cell proliferation in a dose-response manner with an IC50 of about 15 μM for CT1563, the most potent compound tested. This assay is an in vitro model for autoimmune disorders and immunosuppression.

This example illustrates the effects of four inventive compounds on inhibition of murine lymph node cell proliferation stimulated by antigen. This assays uses murine T cells that proliferate in vitro in response to a soluble protein antigen that is first used to prime the T cells in vivo. Drug was added to the cells at the doses indicated two hours prior to activation with alloantigen. Each drug inhibited T cell proliferation in a dose-response manner with an IC50 of about 15 μM for CT1563, the most potent compound tested, as shown in FIG. 11. This assay is an in vitro model for autoimmune disorders and immunosuppression.

Example 44

This example illustrates the effects of four inventive compounds to inhibit proliferation of human lymphocytes in an IL-2 induced blastogenesis in vitro assay. This human in vitro assay is a human model for immune suppression activity to screen for drags that would be beneficial in preventing organ rejection in organ transplantation. Briefly, human lymphocytes are obtained from blood from normal volunteers and plated into wells at 2×10⁵ cells/well. Human IL-2 (40 U/well or 5 μl of a 100 U/ml solution) and drug at various concentrations are added to each well. The cells am incubated for six days and then proliferation is determined by a standard tritiated thymidine incorporation procedure. Cyclosporin A does not show significant activity in this in vitro assay. However, both CT1406 and CT1442 were active, as is shown by IC50 values in FIG. 12.

Example 45

This example illustrates various IC50 values of five inventive compounds as determined by an IL-2 blastogenesis assay described in example 44 above or a CD3 blastogenesis assay. The CD3 blastogenesis assay is virtually identical to the IL-2 blastogenesis assay described herein, except a human anti-CD3 monoclonal antibody (4 μg/ml, Boehinger Manheimm) is used instead of human IL-2 and the cells are incubated for only three days. Again, Cyclosporin A is generally not very active in this in vitro assay. However, as shown in FIG. 13, several inventive compounds, including CT1524, CT2501 and CT2512, showed significant immune suppressing activity in these in vitro assays.

Example 46

This example illustrates the effects of CT2501R (a reference compound), CT2536R, CT2536S, CT1596R, and CT1596S of yeast growth (*Saccromyces cerevasie*) in the presence or absence of drug. These assays measure anti-yeast and anti-fungal activity of the drugs tested. As shown in FIG. 14, both the R and S enantiomers of CT2536 strongly inhibited yeast growth. Therefore either the R enantiomer, the S enantiomer or a racemic mixture of CT2536 are potential topical or systemic antimicrobial drugs. It should be noted that there was enantiomeric selectivity for CT1596.

Example 47

This example illustrates the ability of six inventive compounds to inhibit proliferation of human stromal cells when stimulated with PDGF. This assay is an in vitro model for restenosis and treatment of atherosclerosis and coronary artery disease. Stromal cells were starved in serum-free media for one day and then stimulated with 50 ng/ml PDGF-BB. The drugs were added at the indicated concentrations one hour prior to PDGF stimulation. Tritiated thymidine was added for one day at the time of PDGF stimulation and the cells were harvested and counted by liquid scintillation counting 24 hrs later. Background counts (i.e., starved cells) were approximately 1% of control levels. FIG. 15 shows that all drugs were active in this predictive in vitro model, however CT1403 and CT1411 had IC50 values (μM) less than 10.

FIG. 16 illustrates the ability of eight inventive compounds to inhibit proliferation of human stromal cells when stimulated with PDGF. Background counts (i.e., starved cells) were approximately 1% of control levels. FIG. 16 shows that all drugs were active in this predictive in vitro model, however, CT1508 was most potent with an IC50 value less than 2 μM showing promise as a restenosis and reperfusion injury drug.

Example 48

This example illustrates a comparison of cytotoxicity determinations for CT1534 and CT1539 in transformed cells (Ras 3T3) and in normal 3T3 cells to determine the in vitro LD50 value in both cell types and to look for differential cytotoxicity effects between the cell types. CT1534 was much more cytotoxic for the transformed cell than the normal cell indicating differential toxicity for tumor cells and potential usefulness as a cancer chemotherapeutic agent. CT1539 appeared to be equally cytotoxic for both cell types.

Example 49

This example illustrates data regarding proliferative activity of various inventive compounds for inducting CMV promoter activity. The CMV promoter assay measures gene transcription and translation activity wherein any active compounds will have cytotoxic activity to inhibit cellular protein synthesis machinery in transformed (adenovirus) cells. Each compound was tested and the data is listed in FIG. 18. CT1596S was the most cytotoxic compound tested.

Example 50

This example illustrates a comparative experiment comparing CT1508, CT1524, CT1534 and CT2501 in an ex vivo human TNF model described herein. This assay is a predictive model for treatment and prevention of septic shock and sepsis syndrome. This model adds LPS to whole blood (normal human volunteers) to trigger a dose-dependent synthesis and extracellular release of TNF according to Desch et al. (*Lymphokine Res.* 8:141, 1989). The ex vivo model examines whether LPS-mediated release of TNF from monocytes in whole blood can be blocked by an inventive compound. As shown in FIG. 19, CT1508 was the most effective agent in this ex vivo model for sepsis at lower doses that are likely achievable in vivo.

Example 51

This example illustrates the effect of one inventive compound (CT1534) on the substates and products of the present second messenger pathway. Various concentrations of CT1534 were incubated with P388 cells (a murine monocyte/macrophage line) and changes in lipid mass determined at 0 time, 30 seconds and 60 seconds after signal stimulation. FIGS. 20–22 show the 30 second time point for two DAG peaks and a PA peak. This data shows that CT1534 inhibits the enzymes involved in second messenger signaling to an inflammatory stimulus in a dose-response fashion with a plateau of around 10 µM.

We claim:

1. An olefin-substituted compound having the formula:

R—(core moiety), wherein R is a straight chain hydrocarbon having at least one double bond and a carbon chain length of from about 6 to about 18 carbon atoms, wherein multiple double bonds are separated from each other by at least three carbon atoms, wherein the closest double bond to the core moiety is at least five carbon atoms from the core moiety, wherein the hydrocarbon chain may be substituted by a hydroxyl, keto or dimethylamino group and/or interrupted by an oxygen atom, and wherein the core moiety is a glutarimide, substituted glutarimide, benzoyleneurea, or substituted benzoyleneurea group, wherein substituted glutarimide or benzoyleneurea consists of a hydrogen, methyl, fluoro, chloro or amino group substitution.

2. The olefin-substituted compound of claim 1 wherein R is bonded to a ring nitrogen atom on the core moiety.

3. The olefin-substituted compound of claim 1 which is 1-(5-hexenyl)-3-methylbenzoyleneurea.

4. The olefin-substituted compound of claim 1 which is N-(5-hexenyl)glutarimide.

5. The olefin-substituted compound of claim 1 which is N-(8-nonenyl)glutarimide.

6. The olefin-substituted compound of claim 1 which is N-(6-cis-nonenyl)glutarimide.

7. The olefin-substituted compound of claim 1 which is N-(10-undecenyl)glutarimide.

* * * * *